(12) United States Patent
Farber

(10) Patent No.: US 9,084,780 B2
(45) Date of Patent: *Jul. 21, 2015

(54) ALLANTOIN-CONTAINING SKIN CREAM

(71) Applicant: Scioderm, Inc., Durham, NC (US)

(72) Inventor: Elliott Farber, North Mankato, MN (US)

(73) Assignee: SCIODERM, INC., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/049,831

(22) Filed: Oct. 9, 2013

(65) Prior Publication Data

US 2014/0142151 A1    May 22, 2014

Related U.S. Application Data

(63) Continuation of application No. 13/942,295, filed on Jul. 15, 2013, which is a continuation of application No. 13/645,172, filed on Oct. 4, 2012, now abandoned, which is a continuation of application No. 13/295,890, filed on Nov. 14, 2011, now abandoned, which is a continuation of application No. 13/047,575, filed on Mar. 14, 2011, now abandoned, which is a continuation of application No. 12/172,854, filed on Jul. 14, 2008, now abandoned, which is a continuation of application No. 11/300,360, filed on Dec. 15, 2005, now abandoned, which is a continuation of application No. 09/991,117, filed on Nov. 13, 2001, now abandoned, which is a continuation-in-part of application No. 09/758,781, filed on Jan. 11, 2001, now Pat. No. 6,864,274, which is a continuation-in-part of application No. 09/570,266, filed on May 12, 2000, now Pat. No. 6,329,413, which is a continuation-in-part of application No. 09/360,095, filed on Jul. 23, 1999, now Pat. No. 6,281,236.

(51) Int. Cl.

| A61K 31/4166 | (2006.01) |
|---|---|
| A61K 8/02 | (2006.01) |
| A61K 8/06 | (2006.01) |
| A61K 8/37 | (2006.01) |
| A61K 8/46 | (2006.01) |
| A61K 8/49 | (2006.01) |
| A61K 8/73 | (2006.01) |
| A61K 8/81 | (2006.01) |
| A61K 8/86 | (2006.01) |
| A61K 8/92 | (2006.01) |
| A61K 8/97 | (2006.01) |
| A61K 9/00 | (2006.01) |
| A61K 47/20 | (2006.01) |
| A61K 47/44 | (2006.01) |
| A61Q 17/00 | (2006.01) |
| A61Q 19/00 | (2006.01) |
| A61Q 17/04 | (2006.01) |

(52) U.S. Cl.
CPC .............. *A61K 31/4166* (2013.01); *A61K 8/06* (2013.01); *A61K 8/062* (2013.01); *A61K 8/37* (2013.01); *A61K 8/463* (2013.01); *A61K 8/494* (2013.01); *A61K 8/4946* (2013.01); *A61K 8/73* (2013.01); *A61K 8/8147* (2013.01); *A61K 8/86* (2013.01); *A61K 8/927* (2013.01); *A61K 8/97* (2013.01); *A61K 9/0014* (2013.01); *A61K 47/20* (2013.01); *A61K 47/44* (2013.01); *A61Q 17/00* (2013.01); *A61Q 17/04* (2013.01); *A61Q 19/00* (2013.01); *A61K 2800/5424* (2013.01)

(58) Field of Classification Search
None
See application file for complete search history.

(56) References Cited

U.S. PATENT DOCUMENTS

| 3,830,824 A | 8/1974 | Margraf |
|---|---|---|
| 3,830,825 A | 8/1974 | Margraf |
| 3,830,908 A | 8/1974 | Klippel et al. |
| 3,856,805 A | 12/1974 | Margraf |
| 3,930,000 A | 12/1975 | Margraf |
| 3,932,627 A | 1/1976 | Margraf |

(Continued)

FOREIGN PATENT DOCUMENTS

| EP | 0 030 157 A1 | 6/1981 |
|---|---|---|
| EP | 0 242 553 A1 | 10/1987 |

(Continued)

OTHER PUBLICATIONS

Derwent Abstract for JP 58-140013; original document publication date: Aug. 19, 2013.*

(Continued)

*Primary Examiner* — Sreeni Padmanabhan
*Assistant Examiner* — Jody Karol
(74) *Attorney, Agent, or Firm* — Sterne Kessler Goldstein & Fox P.L.L.C.

(57) ABSTRACT

An allantoin-containing skin cream composition can comprise allantoin and at least one anionic or nonionic emulsifier that is substantially hydrophilic and is soluble in water. The composition is in the form of an oil-in-water emulsion. The pH of the composition is in a range of from about 3.0 to about 6.0; preferably, the pH of the composition is from about 5.0 to about 6.0. The composition can further comprise an acidic anionic polymer. A preferred acidic anionic polymer is a carboxypolymethylene polymer. The composition can further comprise a carbohydrate polymer such as galactoarabinan, polygalactose or polyarabinose. The composition can additionally comprise other ingredients such as herbal extracts, an antioxidant component, an emollient component, a chelator, a solvent component, or a preservative component. The composition is useful as a skin protectant.

20 Claims, No Drawings

(56) References Cited

U.S. PATENT DOCUMENTS

| | | |
|---|---|---|
| 3,954,989 A | 5/1976 | Mecca |
| 4,170,229 A | 10/1979 | Olson |
| 4,184,978 A | 1/1980 | France et al. |
| 4,265,902 A | 5/1981 | Van Ewijk |
| 4,278,664 A | 7/1981 | Van Cleave |
| 4,374,766 A | 2/1983 | Puchalski et al. |
| 4,380,549 A | 4/1983 | Van Scott et al. |
| 4,478,853 A | 10/1984 | Chaussee |
| 4,507,279 A | 3/1985 | Okuyama et al. |
| 4,595,586 A | 6/1986 | Flom |
| 4,670,263 A | 6/1987 | Noorlander |
| 4,707,354 A | 11/1987 | Garlen et al. |
| 4,708,813 A | 11/1987 | Snyder |
| 4,767,618 A | 8/1988 | Grollier et al. |
| 4,806,262 A | 2/1989 | Snyder |
| 4,820,989 A | 4/1989 | Vail, III |
| 4,822,601 A | 4/1989 | Goode et al. |
| 4,880,621 A | 11/1989 | Grollier et al. |
| 4,933,177 A | 6/1990 | Grollier et al. |
| 4,952,560 A | 8/1990 | Kigasawa et al. |
| 4,981,845 A | 1/1991 | Pereira |
| 5,075,626 A | 12/1991 | Vail, III |
| 5,112,886 A | 5/1992 | Phalangas |
| 5,116,829 A | 5/1992 | Hori et al. |
| 5,122,533 A | 6/1992 | Bar-On et al. |
| 5,176,916 A | 1/1993 | Yamanaka et al. |
| 5,221,533 A | 6/1993 | Perlman |
| 5,296,166 A | 3/1994 | Leong |
| 5,326,557 A | 7/1994 | Glover et al. |
| 5,435,996 A | 7/1995 | Glover et al. |
| 5,455,033 A | 10/1995 | Silverman et al. |
| 5,466,718 A | 11/1995 | Nakatsu et al. |
| 5,476,664 A | 12/1995 | Robinson et al. |
| 5,510,712 A | 4/1996 | Sezginer et al. |
| 5,512,200 A | 4/1996 | Garcia |
| 5,536,502 A | 7/1996 | Mulder |
| 5,543,715 A | 8/1996 | Singer et al. |
| 5,563,514 A | 10/1996 | Moulin |
| 5,567,427 A | 10/1996 | Papadakis |
| 5,573,754 A | 11/1996 | Kulkarni et al. |
| 5,578,312 A | 11/1996 | Parrinello |
| 5,608,323 A | 3/1997 | Koelman |
| 5,616,347 A | 4/1997 | Alliger et al. |
| 5,658,559 A | 8/1997 | Smith |
| 5,661,170 A | 8/1997 | Chodosh |
| 5,709,847 A | 1/1998 | Bissett et al. |
| 5,736,128 A | 4/1998 | Chaudhuri et al. |
| 5,753,245 A | 5/1998 | Fowler et al. |
| 5,824,666 A | 10/1998 | Deckner et al. |
| 5,827,870 A | 10/1998 | Chodosh |
| 5,830,483 A | 11/1998 | Seidel et al. |
| 5,849,310 A | 12/1998 | Trinh et al. |
| 5,863,548 A | 1/1999 | Elder |
| 5,871,754 A | 2/1999 | Briggs et al. |
| 5,871,762 A | 2/1999 | Venkitaraman et al. |
| 5,876,736 A | 3/1999 | Cohen et al. |
| 5,885,581 A | 3/1999 | Massand |
| 5,914,116 A | 6/1999 | Suares et al. |
| 5,932,228 A | 8/1999 | Hall et al. |
| 5,952,373 A | 9/1999 | Lanzendörfer et al. |
| 5,958,436 A | 9/1999 | Hahn et al. |
| 5,968,528 A | 10/1999 | Deckner et al. |
| 6,001,377 A | 12/1999 | SaNogueira, Jr. et al. |
| 6,025,721 A | 2/2000 | Vail, III |
| 6,060,061 A | 5/2000 | Breton et al. |
| 6,077,520 A | 6/2000 | Tominaga |
| 6,080,393 A | 6/2000 | Liu et al. |
| 6,086,903 A | 7/2000 | Trinh et al. |
| 6,120,782 A | 9/2000 | Mansouri |
| 6,169,114 B1 | 1/2001 | Yamaguchi et al. |
| 6,174,533 B1 | 1/2001 | SaNogueira, Jr. et al. |
| 6,246,240 B1 | 6/2001 | Vail, III |
| 6,281,236 B1 | 8/2001 | Farber |
| 6,306,915 B1 | 10/2001 | Murata |
| 6,329,413 B1 | 12/2001 | Farber |
| 6,337,065 B1 | 1/2002 | Jacobson et al. |
| 6,351,129 B1 | 2/2002 | Gounot |
| 6,355,259 B1 | 3/2002 | Hiraki et al. |
| 6,531,500 B2 | 3/2003 | Farber |
| 6,545,477 B1 | 4/2003 | Beguin et al. |
| 6,645,507 B2 | 11/2003 | Bettle et al. |
| 6,673,826 B2 | 1/2004 | Farber |
| 6,765,387 B2 | 7/2004 | Prammer |
| 6,864,274 B2 | 3/2005 | Farber |
| 6,896,897 B2 | 5/2005 | Farber |
| 2001/0002290 A1 | 5/2001 | Farber |
| 2001/0003753 A1 | 6/2001 | Farber |
| 2002/0054895 A1 | 5/2002 | Farber |
| 2002/0055531 A1 | 5/2002 | Farber |
| 2002/0102288 A1 | 8/2002 | Farber |
| 2003/0012784 A1 | 1/2003 | Farber |
| 2003/0044435 A1 | 3/2003 | Bettle et al. |
| 2003/0122547 A1 | 7/2003 | Prammer |
| 2003/0129747 A1 | 7/2003 | Frisen |
| 2003/0147968 A1 | 8/2003 | Farber |
| 2003/0157137 A1 | 8/2003 | Farber |
| 2003/0162821 A1 | 8/2003 | Farber |
| 2004/0082634 A1 | 4/2004 | Farber |
| 2004/0180853 A1 | 9/2004 | Farber |
| 2006/0093636 A1 | 5/2006 | Farber |
| 2006/0134149 A1 | 6/2006 | Farber |
| 2008/0075747 A1 | 3/2008 | Farber |
| 2008/0269308 A1 | 10/2008 | Farber |
| 2009/0170919 A1 | 7/2009 | Farber |
| 2011/0152335 A1 | 6/2011 | Farber |
| 2011/0165260 A1 | 7/2011 | Farber |
| 2012/0065238 A1 | 3/2012 | Farber |
| 2012/0165379 A1 | 6/2012 | Farber |
| 2013/0030030 A1 | 1/2013 | Farber |
| 2013/0345274 A1 | 12/2013 | Farber |
| 2014/0005242 A1 | 1/2014 | Farber |
| 2014/0010771 A1 | 1/2014 | Farber |

FOREIGN PATENT DOCUMENTS

| | | |
|---|---|---|
| EP | 0 380 157 A1 | 8/1990 |
| EP | 0 487 404 A1 | 11/1991 |
| EP | 1 004 289 A2 | 11/1999 |
| EP | 2 172 106 A1 | 4/2010 |
| FR | 2 405 068 A1 | 5/1979 |
| GB | 1 202 635 | 8/1970 |
| GB | 1 346 544 | 2/1974 |
| JP | 58-140013 A | 8/1983 |
| JP | 63-159317 A | 7/1988 |
| JP | 64-58165 A | 3/1989 |
| JP | 4-208219 A | 7/1992 |
| WO | WO 90/09779 A1 | 9/1990 |
| WO | WO 98/02138 A1 | 1/1998 |
| WO | WO 98/29085 A2 | 7/1998 |
| WO | WO 00/79307 A1 | 12/2000 |
| WO | WO 01/06991 A1 | 2/2001 |
| WO | WO 01/87232 A2 | 11/2001 |
| WO | WO 01/87301 A1 | 11/2001 |
| WO | WO 03/017941 A2 | 3/2003 |
| WO | WO 03/041651 A2 | 5/2003 |
| WO | WO 03/041688 A1 | 5/2003 |
| WO | WO 03/054585 A1 | 7/2003 |

OTHER PUBLICATIONS

Brust, M.D. and Lin, A.N., "Epidermolysis bullosa: practical management and clinical update" *Dermatol. Nursing* 8(2):81-89, Dermatology Nurses' Association, United States (1996).

Cahen, R. and Pessonnier, A., "Etude pharmacologique de l'allantoïnate de dihydroxyaluminium et de l'allantoïnate de chlorhydroxyaluminium. I.—*Toxicité*," *Annales Pharm. Franç.* 20:623-636, Masson et Cie, France (1962).

Cahen, R. and Clement, J.-F., "Etude pharmacologique de l'allantoïnate de dihydroxyaluminium et de l'allantoïnate de chlorhydroxyaluminium. II.—*Etude de l'activité gastrique,*" *Annales Pharm. Franç.* 20:693-703, Masson et Cie, France (1962).

(56) References Cited

OTHER PUBLICATIONS

Cahen, R. and Pessonnier, A., "Etude pharmacologique de l'allantoïnate de dihydroxyaluminium et de l'allantoïnate de chlorhydroxyaluminium. III.—*Effet anti- ulcéreux,*" *Annales Pharm. Franç.* 20:704-713, Masson et Cie, France (1962).

Cahen, R. and Pessonnier, A., "Etude pharmacologique de l'allantoïnate de dihydroxyaluminium et de l'allantoïnate de chlorhydroxyaluminium. IV.—*Effet sur l 'ulcére médicamenteux expérimental,*" *Annales Pharm. Franç.* 21:215-222, Masson et Cie, France (1963).

Čajkovac, M., et al., "Influence of emulsoid vehicle on the release and activity of allantoin," *Pharmazie* 47:39-43, Govi-Verlag Pharmazautischer Verlag, Germany (1992) (Abstract).

"Chapter 34: Instrumental Methods of Analysis," in *Remington: The Science and Practice of Pharmacy*, 19th Ed., Gennaro, A.R., ed., pp. 639-640,1380, John Wiley & Sons Australia, Limited, Australia (1995).

Debray, CH., et al., "Étude de Dérivés Allantoïniques de l'Aluminium dans la Thérapeutique des Affections Gastro-duodénales," *Presse Méd.* 70:2643-2644, Masson et Cie, France (1962).

Greenbaum, F.R., "The Story of Allantoin," *Am. J. Pharm.* 112:205-216, Philadelphia College of Pharmacy and Science, United States (1940).

Hoffman, D., *The Complete Illustrated Holistic Herbal: A Safe and Practical Guide to Making and Using Herbal Remedies*, Elemental Books, pp. 63, 104, United States (1996).

Lesser, M.A., "Allantoin," *Drug and Cosmetic Industry* 42:451-456, 469, The Drug and Cosmetic Industry, United States (1938).

Levan, P., et al., "The Use of Silicones in Dermatology," *California Medicine* 81(3):210-213, California Medical Association, United States (1954).

Lubowe, I.I. and Mecca, S.B., "Allantoin and Aluminum Derivatives in Dermatological Applications," *Drug and Cosmetic Industry* 84: 36, 37, 117, The Drug and Cosmetic Industry, United States (1959).

Maragakis, M., et al., "Possibilities of Scar Treatment After Thoracic Surgery," *Drugs Exp. Clin.Res.* 21:199-206, (1995), Abstract, 1 Page, accessed at http://www.paperchase.com/scripts/mgwms32.d11/ on Oct. 4, 2011.

Margraf, H.W. and Covey, Jr., T.H., "A Trial of Silver-Zinc-Allantoinate in the Treatment of Leg Ulcers," *Arch Surg* 112:699-704, American Medical Association, United States (1977).

Mecca, S.B., "Allantoin and the Newer Aluminum Allantoinates," *Proc. Scient. Sect. Toilet Goods Assoc.* 31:1-6, The Toilet Goods Association, United States (1959).

Mecca, S.B., "The Function and Applicability of the Allantoins," *Proc. Scient. Sect. Toilet Goods Assoc.* 39:7-15, The Toilet Goods Association, United States (1963).

*The Merck Index: An Encyclopedia of Drugs, Chemicals and Biologicals*, Twelfth Edition, Smith, A., et al., Eds., pp. 128, 735, 1213, Merck & Company, Inc., United States (1996).

National Institute of Standards and Technology, Material Measurement Laboratory, Standard Reference Data Program, CAS RN 99-76-3 and CAS RN 94-13-3, U.S. Secretary of Commerce on behalf of the United States of America (2011).

Alphosyl Cream and Alphosyl Lotion Product Information, South African Electronic Package Inserts, Stafford-Miller Ltd, England (1975).

Arola Rose Balm Product Information, South African Electronic Package Inserts, Pharmaceutical Enterprises (Pty) Ltd, South Africa (1993).

Arola Rosebaum Product Information, Supramed Limited, (1986).

Clearasil Medicated Facial Cleanser Product Information, South African Electronic Package Inserts, Procter & Gamble SA (Pty) Ltd., South Africa (1994).

Stinco, G., et al., "Dermatite seborroica del volto trattata con una crema a base di furalglucitolo," *Derm. Clin.* 18:78-81, Centro Italiano Congressi, Italy (1998).

Westman, M., "Galactoarabinan: An Exfoliant for Human Skin," *Cosmetics and Toiletries* 114(8):63-72, Allured Publishing Corp., United States (1999) (Abstract).

Willital, G.H. and Heine, H., "Efficiency of Contractubex® Gel in the Treatment of Fresh Scars After Thoracic Surgery in Children and Adolescents," *Int. J. Clin. Pharmacol. Res.* 14(5/6):193-202, Bioscience Ediprint Inc., Switzerland (1994).

International Search Report dated Oct. 12, 2000 for PCT/US00/19859.

International Search Report dated Aug. 24, 2001 for PCT/US01/14899.

International Search Report dated Oct. 24, 2001 for PCT/US01/15102.

International Search Report dated Jan. 31, 2003 for PCT/US02/36438.

International Search Report dated Jun. 3, 2003 for PCT/US02/26928.

International Search Report dated Jul. 14, 2003 for PCT/US02/36439.

Supplementary European Search Report dated Nov. 26, 2004 for EP 00 95 0494.

European Search Report dated Feb. 24, 2010 for EP 07 02 1279.

Almeyda, J., et al., "Treatment of Psoriasis: Comparative Study Using Allantoin Coal Tar Extract Combined with Hydrocortisone and Betamethasone Valerate," *Brit. J. Clin. Pract.* 33(4):106-108, Harvey & Blythe Ltd., England (1979).

Berthemy, A., et al., "Quantitative determination of an extremely polar compound allantoin in human urine by LC-MS/MS based on the separation on a polymeric amino column," *J. Pharm. Biomed. Anal.* 19:429-434, Elservier Science B.V., England (1999).

Brookes, D.B., et al., "Comparison of Tretinoin and a Composite Formulation in the Treatment of Acne," *Brit. J. Clin. Pract.* 32(12):349-352, Harvey & Blythe Ltd., England (1978).

Castro, A H. F., et al., "Influence of Photoperiod on the Accumulation of Allantoin in Comfrey Plants," *R. Bras. Fisiol. Veg.* 13(1):49-54, Sociedade Brasileira de Fisiologia Vegetal, Brazil (2001).

Fisher, A. A., "Allantoin: A Non-Sensitizing Topical Medicament Therapeutic Effects of the Addition of 5 Percent Allantoin to Vaseline," *Cutis* 27:230-234, Cahners Pub. Co., United States (1981).

Fraser, N. B., et al., "Treatment of acne vulgaris comparing two similar lotion formulations, one with ('Actinac') and one without chloramphenicol," *Curr. Med. Res. Opin.* 6(7):461-465, M. D. Promotions, ltd., United Kingdom (1980).

Garnik, J. J., et al., "Effectiveness of a medicament containing silicon dioxide, aloe, and allantoin on aphthous stomatitis," *Oral. Surg. Oral. Med. Oral. Pathol. Oral. Radiol. Endod.* 86(5):550-556, Elsevier, United States (1998).

Harrington, C. I., "Low concentration dithranol and coal tar (Psorin) in psoriasis: a comparison with alcoholic coal tar extract and allantoin (Alphosyl)," *Brit. J. Clin. Pract.* 43(1):27-29, Harvey & Blythe Ltd., England (1989).

Henning, T., "Evaluation of the Efficacy of Allantoin," *Euro. Cosmet.* 2:20-22 (2001).

Kaplan, T., "The Allantoin Treatment of Ulcers," *JAMA* 108(12):968-969, American Medical Association, United States (1937).

Klippel, A. P., et al. , "The Use of Silver-Sinc-Allantoin Powder for the Prehospital Treatment of Burns," *JACEP* 6(5):184-186, American College of Emergency Physicians, United States (1966).

Lunan, H.N., "Topical treatment of the burn patient," *Am. J. Hosp. Pharm.* 32:599-605, American Society of Hospital Pharmacists, Inc., United States (1975).

Meixell, D. W., et al., "The Allantoins," *J. Am. Podiatry Assoc.* 56(8):357-364, American Podiatry Association, United States (1966).

Parish, L. C., el al . , "Oxipor VHC Lotion Versus Tegrin in the Treatment of Psoriasis," *Cutis* 30(5):676-678, Quadrant HealthCom Inc., United States (1982).

Pavillard, E. R., et al., "An Antibiotic from Maggots," *Nature* 180:916-917, Nature Publishing Group, England (1957).

Pavitt, D. V., et al., "Assay of serum allantoin in humans by gas chromatography-mass spectrometry," *Clinica. Chimica. Acta.* 318:63-70, Elsevier, Netherlands (2002).

(56) References Cited

OTHER PUBLICATIONS

Robinson, W., "Stimulation of Healing in Non-Healing Wounds: By Allantoin Occurring in Maggot Secretions and of Wide Biological Distribution," *J. Bone Joint Surg. Am.* 17:267-271, The Journal of Bone and Joint Surgery, United States (1935).

Sheker, K. M., et al., "Silver Allantoinate for the Topical Treatment of Burns," *Am. J. Hosp. Pharm.* 29:852-855, American Society of Hospital Pharmacists, United States (1972).

Thompson, J. E., et al., "Topical Use of Aloe Vera Derived Allantoin Gel in Otolaryngology," *Ear Nose Throat J.* 70(1):56, Medquests Communications, United States (1991).

Van Der Cammen, T. J. M., et al., "Prevention of pressure sores. A comparison of new and old pressure sore treatments," *Brit. J Clin. Pract.* 41(11):1009-1011, Harvey & Blythe Ltd., England (1987).

Wadhams, P. S., et al., "Efficacy of a Surfactant, Allantoin, and Benzalkonium Chloride Solution for Onychomycosis: Preliminary Results of Treatment with Periodic Debridement," *J. Am. Podiatr. Med. Assoc.* 89(3):124-130, American Podiatry Association, United States (1999).

Young, E. G., et al., "The Estimation of Allantoin in Blood," *J. Biol. Chem.* 152:245-253, American Society for Biochemistry and Molecular Biology, United States (1944).

Young, E., "Allantoin in Treatment of Psoriasis," *Dermatologica* 147(5):338-341, Karger, Switzerland (1973).

"Committee for Veterinary Medical Products—Allantoin—Summary Report," EMEA/MRL/804/01-Final, Oct. 2001, The European Agency for Evaluation of Medicinal Products Veterinary Medicines and Inspections (EMEA), United Kingdom (2001).

Office Action mailed Apr. 8, 2013, in U.S. Appl. No. 13/019,039, inventor Elliot Farber, filed Feb. 1, 2011.

Office Action mailed Jan. 24, 2014, in U.S. Appl. No. 13/019,039, inventor Elliot Farber, filed Feb. 1, 2011.

Office Action mailed Dec. 3, 2013, in U.S. Appl. No. 13/942,295, inventor Elliot Farber, filed Jul. 15, 2013.

Office Action mailed Dec. 3, 2013, in U.S. Appl. No. 14/018,050, inventor Elliot Farber, filed Sep. 4, 2013.

Office Action mailed Dec. 3, 2013, in U.S. Appl. No. 14/018,167 inventor Elliot Farber, filed Sep. 4, 2013.

Supplementary European Search Report for EP 01 93 5174, European Patent Office, Germany, dated Dec. 17, 2004.

Co-pending Unpublished Application, U.S. Appl. No. 13/019,039, inventor Elliott Farber, filed on Feb. 1, 2011 (NOT PUBLISHED).

Co-pending Unpublished Application, U.S. Appl. No. 14/062,295, inventor Elliott Farber, filed on Oct. 24, 2013 (NOT PUBLISHED).

Co-pending Unpublished Application, U.S. Appl. No. 14/147,425, inventor Elliott Farber, filed on Jan. 3, 2014 (NOT PUBLISHED).

\* cited by examiner

ALLANTOIN-CONTAINING SKIN CREAM

CROSS REFERENCES

This application is a continuation of U.S. application Ser. No. 13/942,295, filed Jul. 15, 2013, which is a continuation of U.S. application Ser. No. 13/645,172, filed Oct. 4, 2012, now abandoned, which is a continuation of U.S. application Ser. No. 13/295,890, filed Nov. 14, 2011, now abandoned, which is a continuation of U.S. application Ser. No. 13/047,575, filed Mar. 14, 2011, now abandoned, which is a continuation of U.S. application Ser. No. 12/172,854, filed Jul. 14, 2008, now abandoned, which is a continuation of U.S. application Ser. No. 11/300,360, filed Dec. 15, 2005, now abandoned, which is a continuation of U.S. application Ser. No. 09/991,117, filed Nov. 13, 2001, now abandoned, which is a continuation-in-part of U.S. application Ser. No. 09/758,781, filed Jan. 11, 2001 and issued as U.S. Pat. No. 6,864,274, which is a continuation-in-part of U.S. application Ser. No. 09/570,266, filed May. 12, 2000 and issued as U.S. Pat. No. 6,329,413, which is a continuation-in-part of U.S. application Ser. No. 09/360,095, filed Jul. 23, 1999 and issued as U.S. Pat. No. 6,281,236, each of which is incorporated in their entirety by reference herein.

BACKGROUND OF THE INVENTION

1. Field of the Invention

This invention is directed to a skin cream containing allantoin in an oil-in-water emulsion with improved stability.

2. General Background and State of the Art

Allantoin is a commonly used ingredient in cosmetic applications, particularly for skin creams, where it exerts a skin protective function. Many such cosmetic compositions and other compositions are prepared as emulsions, particularly oil-in-water emulsions. One emulsifier system used with such compositions is a combination of sodium lauryl sulfate and beeswax. Although solutions of sodium lauryl sulfate are alkaline with an approximate pH of 9.5, the simultaneous use of beeswax with its organic acids produces a complex and neutralized system with a pH of about 6.8 to about 7.5. However, in such a system with a pH range of 6.8 to 7.5, allantoin degrades significantly with time and in accelerated stability tests at 40° C. Because cosmetics and other preparations designed for application to the skin are typically stored by users at room temperature, and room temperatures can fluctuate with climatic conditions, such a degree of stability is undesirable. Therefore, there is a need for an oil-in-water emulsified composition containing allantoin in which the stability of allantoin is increased.

In particular, there is a need for compositions that are suitable for treating a number of severe and difficult-to-treat skin conditions. One of these skin conditions is epidermolysis bullosa. This is a severe genetic skin disorder in which the skin breaks down and large blisters appear. These blisters are difficult to treat by conventional means. Other skin diseases for which improved treatments are needed are pressure ulcers, decubitus ulcers or bed sores, and diabetic ulcers, and milia, as well as other conditions affecting the skin and having an inflammatory component such as eczema, urticaria, atopic dermatitis, contact dermatitis, arthritis, gout, and lupus erythematosus. Therefore, improved compositions that are suitable for treating these diseases are needed.

INVENTION SUMMARY

In general, a composition according to the present invention comprises an oil-in-water emulsion comprising:
(1) allantoin; and
(2) at least one anionic or nonionic emulsifier that is substantially hydrophilic and is soluble in water.

The pH of the composition is in a range of from about 3.0 to about 6.0. This pH range stabilizes the allantoin and makes storage of the composition for extended periods practical. Preferably, the pH of the composition is in a range of from about 5.0 to about 6.0.

Typically, the at least one anionic or nonionic emulsifier is selected from the group consisting of:
(1) an acidic anionic polymer;
(2) an anionic emulsifier selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate;
(3) a nonionic emulsifier that is an ethoxylated ether or an ethoxylated ester whose chain length ranges from 8 to 22 carbon atoms;
(4) glyceryl stearate;
(5) cetyl alcohol;
(6) stearic acid;
(7) sodium stearoyl lactylate;
(8) sodium isostearoyl lactylate;
(9) triethanolamine stearate;
(10) a polyethylene glycol ether of cetearyl alcohol wherein the number of polyethylene glycol moieties in the ether is from 6 to 40; and
(11) an acidic wax.

The composition can further comprise a carbohydrate polymer selected from the group consisting of galactoarabinan, polygalactose, and polyarabinose. Typically, the carbohydrate polymer is galactoarabinan.

Acidic waxes are those waxes having acidic groups that can be neutralized with alkaline materials such as hydroxides, alkoxides, unprotonated amines, and/or salts of strong bases and weak acids, such as sodium acetate. Upon neutralization, such waxes can act as emulsifiers or coemulsifiers. Particularly preferred acidic waxes include beeswax, carnauba wax, candelilla wax, siliconyl beeswax, siliconyl carnauba wax, and synthetic acidic waxes. A particularly preferred acidic wax is beeswax.

One embodiment of the present invention is a composition comprising an oil-in-water emulsion comprising:
(1) allantoin; and
(2) an emulsifier system comprising:
(a) an acidic anionic polymer; and
(b) a polyethylene glycol ester of stearic acid.

The pH of the composition is from about 3.0 to about 6.0. Preferably, the pH of the composition is from about 5.0 to about 6.0.

Typically, in this embodiment, the acidic anionic polymer is a carboxypolymethylene polymer.

The composition can further comprise a carbohydrate polymer. Typically, the carbohydrate polymer is selected from the group consisting of galactoarabinan, polygalactose, and polyarabinose. Preferably, the carbohydrate polymer is galactoarabinan.

Another embodiment of the present invention is a composition comprising an oil-in-water emulsion comprising:
(1) allantoin; and
(2) an emulsifier system comprising:
(a) an acidic anionic polymer; and
(b) an anionic emulsifier that is substantially hydrophilic and is soluble in water, the pH of the composition being adjusted to a range of from about 3.0 to about 6.0. Preferably, the pH of the composition is adjusted to a range of from about 5.0 to about 6.0.

The anionic emulsifier can be selected from the group consisting of sodium lauryl sulfate, sodium laureth sulfate, sodium oleyl succinate, sodium dodecylbenzenesulfonate, and sodium lauryl sarcosinate. Preferably, the anionic emulsifier is sodium lauryl sulfate.

The composition can further comprise a carbohydrate polymer selected from the group consisting of galactoarabinan, polygalactose and polyarabinose. Preferably, the carbohydrate polymer is galactoarabinan.

Another embodiment of the present invention is a composition comprising an oil-in-water emulsion comprising:
(1) allantoin;
(2) an emulsifier system comprising an acidic anionic polymer; and
(3) a base to adjust the pH of the composition to a value in a range from about 3.0 to about 6.0. Preferably, the pH of the composition is from about 5.0 to about 5.5.

Preferably, the acidic anionic polymer is a carboxypolyethylene polymer. Preferably, the base is an organic base such as triethanolamine.

In another embodiment, the composition comprises an oil-in-water emulsion comprising:
(1) allantoin;
(2) an emulsifier system comprising:
  (a) an acidic anionic polymer; and
  (b) a nonionic emulsifier that is an ethoxylated ether or an ethoxylated ester whose carbon chain length ranges from 8 to 22 carbon atoms, wherein the pH of the composition is from about 3.0 to about 6.0. Preferably, the pH of the composition is from about 5.0 to about 6.0.

In this embodiment, the emulsifier system can further comprise glyceryl stearate.

This embodiment also can include a carbohydrate polymer as described above.

In yet another embodiment of the present invention, a composition comprising an oil-in-water emulsion comprising:
(1) allantoin;
(2) an emulsifier system comprising:
  (a) sodium stearoyl lactylate;
  (b) sodium isostearoyl lactylate;
  (c) optionally, triethanolamine stearate;
  (d) optionally, at least one nonionic emulsifier selected from the group consisting of a nonionic emulsifier that is an ethoxylated ether or an ethoxylated ester whose carbon chain length ranges from 8 to 22 carbon atoms; and
(3) an acid to adjust the pH to a range of from about 3.0 to about 6.0. Preferably, the pH is adjusted to a range of from about 5.0 to about 5.8.

Typically, the acid is citric acid.

Still another embodiment of the present invention is a composition comprising an oil-in-water emulsion comprising:
(1) allantoin; and
(2) an emulsifier system comprising at least one polyethyleneglycol ether of cetearyl alcohol, wherein the number of polyethylene glycol moieties in the polyethyleneglycol ether of cetearyl alcohol is from 6 to 40; and
(3) an acid to adjust the pH of the composition to a range of from about 5.0 to about 5.8.

For this embodiment, the acid is typically also citric acid.

For this embodiment, the emulsifier system typically comprises ceteareth-25 and ceteareth-6.

Yet another embodiment of the present invention is a composition comprising an oil-in-water emulsion comprising:
(1) allantoin;
(2) an emulsifier system comprising:
  (a) a polyethylene glycol ester of stearic acid; and
  (b) glyceryl stearate; and
(3) an acid to adjust the pH of the composition to a range of from about 3.0 to about 6.0. Preferably, the pH is adjusted to a range of from about 5.0 to about 5.8.

Typically, in this embodiment, the number of ethylene glycol moieties in the polyethylene glycol ester of stearic acid is from 25 to 100. Preferably, the polyethylene glycol ester of stearic acid is PEG-100 stearate. Typically, in this embodiment, the acid is citric acid.

Still another embodiment of the present invention is a composition comprising an oil-in-water emulsion comprising:
(1) allantoin;
(2) a carbohydrate polymer; and
(3) an emulsifier system comprising:
  (a) an acidic wax; and
  (b) an anionic emulsifier that is substantially hydrophilic and is soluble in water;

The pH of the composition is in a range from about 3.0 to about 6.0. Preferably, the pH is in the range of from about 5.0 to about 6.0.

The carbohydrate polymer in this embodiment is as described above.

Typically, the anionic emulsifier that is substantially hydrophilic and soluble in water is selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate. Preferably, the anionic emulsifier is sodium lauryl sulfate.

The acidic wax in this embodiment is as described above. Typically, the acidic wax is beeswax, carnauba wax, candelilla wax, siliconyl beeswax, siliconyl carnauba wax, or a synthetic acidic wax. Preferably, the acidic wax is beeswax.

The composition can further comprise citric acid to adjust the pH.

Still another embodiment of the present invention is a composition comprising an oil-in-water emulsion comprising:
(1) allantoin in a concentration of at least about 2.5% and;
(2) an emulsifier system comprising:
  (a) an acidic wax; and
  (b) an anionic emulsifier that is substantially hydrophilic and is soluble in water.

The pH of the composition is in a range from about 3.0 to about 6.0.

Typically, the anionic emulsifier that is substantially hydrophilic and soluble in water is selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate. Preferably, the anionic emulsifier is sodium lauryl sulfate.

The acidic wax in this embodiment is as described above. Typically, the acidic wax is beeswax, carnauba wax, candelilla wax, siliconyl beeswax, siliconyl carnauba wax, or a synthetic acidic wax. Preferably, the acidic wax is beeswax.

The composition can further comprise citric acid to adjust the pH.

For all of these embodiments, the composition can comprise one or more additional ingredients as described below.

The composition can comprise an emollient component comprising at least one emollient selected from the group consisting of lanolin oil, cetyl alcohol, stearyl alcohol, and cod liver oil.

The composition can comprise an emollient such as butylated hydroxytoluene.

The composition can comprise herbal extracts such as one or more of St John's wort extract, witch hazel extract, chamomile extract, and arnica extract.

The composition can comprise a preservative component comprising at least one preservative selected from the group consisting of methylparaben, propylparaben, and diazolidinyl urea.

The composition can comprise a chelating agent such as tetrasodium EDTA.

The composition can comprise a solvent component comprising at least one solvent selected from the group consisting of propylene glycol, butylene glycol and glycerin. Preferably, the solvent component is propylene glycol.

Ranges of compositions are disclosed for each of these embodiments.

DETAILED DESCRIPTION OF THE PREFERRED EMBODIMENTS

A composition according to the present invention comprises an oil-in-water emulsion comprising:
(1) allantoin; and
(2) at least one anionic or nonionic emulsifier that is substantially hydrophilic and is soluble in water.

The composition can further include other ingredients, such as a chelating agent to bind metal ions that might accelerate degradation of the composition. A particularly preferred chelating agent is EDTA. The EDTA can be added in various acid or salt forms depending on the pH of the composition, such as EDTA itself, disodium EDTA, or tetrasodium EDTA.

The pH of the composition is in a range of from about 3.0 to about 6.0. This pH range stabilizes the allantoin and makes storage of the composition for extended periods practical. Preferably, the pH is in a range of from about 5.0 to about 6.0. In some cases, depending on the ingredients used in the composition, narrower pH ranges, such as from about 5.0 to about 5.8, or from about 5.0 to about 5.5, are desirable.

Typically, the at least one anionic or nonionic emulsifier is selected from the group consisting of:
(1) an acidic anionic polymer;
(2) an anionic emulsifier selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate;
(3) an nonionic emulsifier that is an ethoxylated ether or an ethoxylated ester whose chain length ranges from 8 to 22 carbon atoms;
(4) glyceryl stearate;
(5) cetyl alcohol;
(6) stearic acid;
(7) sodium stearoyl lactylate;
(8) sodium isostearoyl lactylate;
(9) triethanolamine stearate;
(10) a polyethylene glycol ether of cetearyl alcohol wherein the number of polyethylene glycol moieties in the ether is from 6 to 40; and
(11) an acidic wax.

The composition can further comprise a carbohydrate polymer selected from the group consisting of galactoarabinan, polygalactose, and polyarabinose. Typically, the carbohydrate polymer is galactoarabinan.

Acidic waxes are those waxes having acidic groups that can be neutralized with alkaline materials such as hydroxides, alkoxides, unprotonated amines, and/or salts of strong bases and weak acids, such as sodium acetate. Upon neutralization, such waxes can act as emulsifiers or coemulsifiers. Particularly preferred acidic waxes include beeswax, carnauba wax, candelilla wax, siliconyl beeswax, siliconyl carnauba wax, and synthetic acidic waxes. Examples of synthetic acidic waxes are syncrowaxes marketed by Croda, Inc.

One embodiment of an improved composition containing allantoin is a composition that comprises an oil-in-water emulsion comprising
(1) allantoin; and
(2) an emulsifier system comprising:
(a) an acidic anionic polymer; and
(b) a polyethylene glycol ester of stearic acid.

The pH of the composition is adjusted to a range of from about 3.0 to about 6.0. Preferably, the pH is adjusted to a range of from about 5.0 to about 6.0. The pH is adjusted with sodium hydroxide or another base as required.

The acidic anionic polymer is preferably a carboxypolymethylene polymer. Such polymers are marketed under the brand names "Carbomer" and "Carbopol." A suitable carboxypolymethylene polymer is marketed by B.F. Goodrich under the brand name "Carbomer." This is a slightly cross-linked polyacrylic acid that is from 1% to 2% cross-linked by allylsucrose or allylpentaerythritol with the polyacrylic acid. The resulting molecular weight range of this polymer is from about $2\times10^6$ daltons to about $1\times10^9$ daltons. The average molecular weight of this polymer is about $4\times10^6$ daltons.

Preferably, the concentration of the carboxypolymethylene polymer is from about 0.5 percent to about 2 percent of the composition.

The composition can further comprise a carbohydrate polymer. Preferably, the carbohydrate polymer is galactoarabinan. Galactoarabinan is derived from trees of the genus *Larix* (larch) and is a hemicellulosic product easily extractable by water in a pure form. Galactoarabinan has been consumed by humans in common foods such as carrots, tomatoes, maple syrup, soybeans, and wheat flour, among others. The molecular weight of the galactoarabinan is about 20,000. A suitable source of galactoarabinan is Larex, Inc. (White Bear Lake, Minn.). Typically, the composition contains from about 1 percent to about 25 percent of galactoarabinan. Preferably, the composition contains from about 2 percent to about 10 percent of the carbohydrate polymer.

This embodiment of a composition according to the present invention can further include other ingredients. For example, the composition can include an emollient component for smoothness. The emollient component can include at least one emollient selected from the group consisting of lanolin oil, cetyl alcohol, stearyl alcohol, and cod liver oil.

The composition can also include an antioxidant to prevent rancidity of ingredients such as cod liver oil. A preferred antioxidant is butylated hydroxytoluene (BHT). Other antioxidants such as butylated hydroxyanisole (BHA) can be used, alternatively or in addition to BHT.

The composition can further include a solvent component. Typically, the solvent component can include at least one solvent selected from the group consisting of ethylene glycol, propylene glycol, glycerin, or butylene glycol. Preferably, the solvent component is propylene glycol.

The composition can further include a preservative component. The preservative component can comprise at least one preservative selected from the group consisting of methylparaben, propylparaben, and diazolidinyl urea. Preferably, the preservative component comprises methylparaben, propylparaben, and diazolidinyl urea. Other preservatives can also be used.

The composition can further include fragrance. The use of fragrance is well known in the cosmetic art and in the art of over-the-counter drug formulation, and many suitable fragrances are known in the art. The stability and function of the cream is not altered by the presence or absence of fragrance.

Optionally, this embodiment of the composition can further include herbal extracts. The herbal extracts can include one or more of St. John's wort extract, witch hazel extract, chamomile extract, and arnica extract. However, these herbal extracts are typically omitted in this embodiment.

This embodiment of the composition can optionally further include other components, such as proteins, humectants, other preservatives, essential oils, other vitamins, colorants, hydroxyacids, other plant extracts, chelators, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

The following discussion describes ranges, preferred concentrations and optimum concentrations for preferred compositions according to this embodiment of the present invention with a pH range of from about 5.0 to about 6.0. For this and other ranges, preferred concentrations, and optimum concentrations of specific ingredients for other embodiments as given below, all percentages are weight percentages unless otherwise specified.

Water can comprise from about 50.0% to about 90.0% of this embodiment of the composition. Preferably, water comprises from about 60.0% to about 85.0% of this embodiment of the composition. In one alternative, in which the optimum concentration of allantoin is about 1.50% of the composition, the optimum concentration of water is about 69.95% of the composition. In another alternative, in which the optimum concentration of allantoin is about 9.00% of the composition, the optimum concentration of water is about 62.45% of the composition.

The carboxypolymethylene polymer can comprise from about 0.30% to about 3.0% of this embodiment of the composition. Preferably, the carboxypolymethylene polymer comprises from about 0.50% to about 2.0% of this embodiment of the composition. An optimum concentration of the carboxypolymethylene polymer is about 0.85% of this embodiment of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

PEG-100 stearate can comprise from about 0.25% to about 2.5% of this embodiment of the composition. Preferably. PEG-100 stearate comprises from about 0.50% to about 2.0% of this embodiment of the composition. An optimum concentration of PEG-100 stearate is about 1.50% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 8.0% of this embodiment of the composition. A preferred concentration of cetyl alcohol is from about 2.0% to about 7.0% of this embodiment of the composition. An optimum concentration of cetyl alcohol is about 4.20% of this embodiment of the composition.

Stearyl alcohol can comprise from about 0.5% to about 6.0% of this embodiment of the composition. A preferred concentration of stearyl alcohol is from about 0.75% to about 5.0% of this embodiment of the composition. An optimum concentration of stearyl alcohol is about 1.50% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. A preferred concentration of methylparaben is from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Diazolidinyl urea can comprise from about 0.05% to about 0.25% of this embodiment of the composition. Preferably, diazolidinyl urea comprises from about 0.10% to about 0.20% of this embodiment of the composition. An optimum concentration of diazolidinyl urea is about 0.15% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of this embodiment of the composition.

Fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of the composition. As indicated above, fragrance can be omitted, and it may be desirable to omit fragrance in circumstances in which the composition is intended for use on sensitive individuals or individuals who may undergo an allergic reaction to fragrance.

Triethanolamine can comprise from about 0.05% to about 3.0% of this embodiment of the composition to adjust the pH. A preferred concentration of triethanolamine is from about 0.20% to about 2.0% of this embodiment of the composition. An optimum concentration of triethanolamine is about 0.80% of this embodiment of the composition.

In another alternative embodiment of the composition, the emulsifier can be an anionic emulsifier that is substantially hydrophilic and is soluble in water. In this embodiment, the anionic emulsifier replaces the polyethylene glycol ester of stearic acid. This embodiment further includes the acidic anionic polymer such as carboxypolymethylene. Optionally, but preferably, this alternative embodiment of the composition includes the carbohydrate polymer such as galactoarabinan.

The anionic emulsifier that is substantially hydrophilic and soluble in water can be selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate. A particularly preferred anionic emulsifier is sodium lauryl sulfate.

Commercially available preparations of sodium lauryl sulfate contain sufficient excess sodium hydroxide so that they have a pH of about 10.0. This sodium hydroxide can be used to adjust the pH when the anionic emulsifier is sodium lauryl sulfate; in this alternative, no additional alkali may be needed. When another anionic emulsifier is used, additional alkali may be required to adjust the pH.

In yet another alternative embodiment of the composition, the emulsifier system comprises the acidic anionic polymer as described above and a nonionic emulsifier that is an ethoxylated ether or an ethoxylated ester whose carbon chain length ranges from 8 to 22 carbon atoms.

Preferably, the acidic anionic polymer is carboxypolymethylene as described above.

This alternative embodiment of the composition can further include glyceryl stearate in the emulsifier system.

This embodiment of the composition has a pH from about 3.0 to 6.0, adjusted as necessary, typically with an acid. The acid can be an organic acid, an inorganic acid, or a mixture of both. Preferably, the pH is from about 5.0 to about 6.0.

This embodiment of the composition can further comprise a carbohydrate polymer such as galactoarabinan as described above.

In this embodiment of the composition, preferred organic acids include organic acids whose carbon chain length ranges from 2 to 22 carbon atoms and that can be monocarboxylic, dicarboxylic, or tricarboxylic acids. The acids can be aliphatic or aromatic. Particularly preferred organic acids include citric acid, ascorbic acid, glycolic acid, lactic acid, benzoic acid, and salicylic acid. A most particularly preferred organic acid is citric acid.

Typically, in this embodiment of the composition, the inorganic acid is a strong acid. It can be a monoprotic, diprotic, or triprotic acid. Particularly preferred inorganic acids include hydrochloric acid, sulfuric acid, and phosphoric acid.

This alternative embodiment of the composition can further include other ingredients as described above, including an emollient component, an antioxidant, a solvent component, a chelating agent, herbal extracts, a preservative, and fragrance.

The composition can further include other components, such as proteins, humectants, other preservatives, essential oils, other vitamins, colorants, hydroxyacids, other plant extracts, sunscreens, sodium hyaluronate, lipids, fatty acids, thickeners, panthenol, and the like. The use of such components is conventional in the cosmetic art and in the over-the-counter drug art. Typical sunscreens are octyl methoxycinnamate and benzophenone-3.

In yet another embodiment of the composition, the emulsifier system comprises the acidic anionic polymer described above; one example of this acidic anionic polymer is marketed as Carbomer. In this embodiment, the pH is adjusted with an organic or inorganic base to a range of from about 3.0 to about 6.0. Preferably, the pH is adjusted to a range of from about 5.0 to about 5.5. A preferred organic base is triethanolamine. A preferred inorganic base is sodium hydroxide. In general, it is preferred to use an organic base such as triethanolamine.

This embodiment can further comprise other ingredients. For example, this embodiment of the invention can further comprise a solvent component. Typically, the solvent component comprises at least one solvent selected from the group consisting of ethylene glycol, propylene glycol, glycerin, or butylene glycol. Preferably, the solvent component is propylene glycol.

This embodiment of the invention can further comprise an emollient component. The emollient component can comprise at least one solvent selected from the group consisting of lanolin oil, cetyl alcohol, and cod liver oil. Preferably, the emollient component comprises al of lanolin oil, cetyl alcohol, and cod liver oil.

This embodiment of the composition can also include an antioxidant. A preferred antioxidant is butylated hydroxytoluene. As indicated above, other antioxidants such as butylated hydroxyanisole can also be used.

This embodiment of the invention can further comprise a preservative component. The preservative component can comprise at least one preservative selected from the group consisting of methylparaben and propylparaben. Preferably, the preservative component comprises both methylparaben and propylparaben. As indicated above, other preservatives can also be used.

This embodiment of the composition can further include fragrance as described above. The stability and function of the cream are not altered by the presence or absence of fragrance. As indicated above, it may be desirable to omit fragrance in some cases.

The following discussion describes ranges, preferred concentrations and optimum concentrations for preferred compositions according to this embodiment of the present invention where the pH is from about 5.0 to about 5.5.

Water can comprise from about 50.0% to about 90.0% of this embodiment of the composition. Preferably, water comprises from about 60.0% to about 80.0% of this embodiment of the composition. In one alternative, in which the optimum concentration of allantoin is about 1.50% of the composition, an optimum concentration of water is about 73.55% of this embodiment of the composition, in another alternative, in which the optimum concentration of allantoin is about 9.00% of the composition, the optimum concentration of water is about 66.05% of the composition.

The carboxypolymethylene polymer can comprise from about 0.40% to about 3.0% of this embodiment of the composition. Preferably, the carboxypolymethylene polymer comprises from about 0.5% to about 2.0% of this embodiment of the composition. An optimum concentration of the carboxypolymethylene polymer is about 1.00% of the composition.

Propylene glycol can comprise from about 2.0% to about 9.0% of this embodiment of the composition. Preferably, the propylene glycol comprises from about 4.0% to about 7.0% of this embodiment of the composition. An optimum concentration of the propylene glycol is about 5.70% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.0% of this embodiment of the composition.

Cetyl alcohol can comprise from about 1.0% to about 8.0% of this embodiment of the composition. Preferably, cetyl alcohol comprises from about 2.0% to about 7.0% of this embodiment of the composition. An optimum concentration of cetyl alcohol is about 3.00% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.30% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of the composition.

Fragrance, if present, can comprise from about 0.05% to about 0.50% of this embodiment of the composition. Preferably, if present, fragrance comprises from about 0.10% to about 0.40% of this embodiment of the composition. An optimum concentration of fragrance, if present, is about 0.20% of this embodiment of the composition.

Triethanolamine, as a 95% solution, can comprise from about 0.05% to about 3.0% of this embodiment of the composition to adjust the pH to a value in the range of from about 5.0 to about 5.5. Preferably, triethanolamine comprises from about 0.20% to about 2.0% of this embodiment of the composition to adjust the pH as indicated. An optimum concentration of triethanolamine is about 0.80% of the composition to adjust the pH as indicated.

Yet another embodiment of a composition according to the present invention is a composition comprising an oil-in-water emulsion comprising:

(1) allantoin; and
(2) an emulsifier system comprising:
 (a) cetyl alcohol; and
 (b) stearic acid.

In this embodiment, the pH is adjusted to a range of from about 3.0 to about 6.0 by addition of a quantity of a weak organic base. Preferably, the pH is adjusted to a range of from about 5.0 to about 5.8. The weak organic base can be an amine-containing base such as ethanolamine, diethanolamine, or triethanolamine. A preferred organic base is triethanolamine.

This embodiment can further comprise other ingredients. For example, this embodiment of the invention can further comprise a solvent component. Typically, the solvent component comprises at least one solvent selected from the group consisting of ethylene glycol, propylene glycol, glycerin, or butylene glycol. Preferably, the solvent component is propylene glycol.

This embodiment of the invention can further comprise an emollient component. The emollient component can comprise at least one solvent selected from the group consisting of lanolin oil, cetyl alcohol, and cod liver oil. Preferably, the emollient component comprises all of lanolin oil, cetyl alcohol, and cod liver oil.

This embodiment of the composition can also include an antioxidant. A preferred antioxidant is butylated hydroxytoluene. As indicated above, other antioxidants such as butylated hydroxyanisole can also be used.

This embodiment of the invention can further comprise a preservative component. The preservative component can comprise at least one preservative selected from the group consisting of methylparaben and propylparaben. Preferably, the preservative component comprises both methylparaben and propylparaben. As indicated above, other preservatives can alternatively be used.

This embodiment of the composition can further include fragrance as described above. The stability and function of the cream is not altered by the presence or absence of fragrance. As indicated above, it may be desirable to omit fragrance in some cases.

The following discussion describes ranges, preferred concentrations and optimum concentrations for preferred compositions according to this embodiment of the present invention when the pH is in the range of from about 5.0 to about 5.8.

Water can comprise from about 50.0% to about 90.0% of this embodiment of the composition. Preferably, water comprises from about 60.0% to about 85.0% of this embodiment of the composition. In one alternative, in which the optimum concentration of allantoin is about 1.50% of the composition, the optimum concentration of water is about 71.70% of the composition. In another alternative, in which the optimum concentration of allantoin is about 9.00% of the composition, the optimum concentration of water is about 64.20% of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

Triethanolamine can comprise from about 0.2% to about 4.0% of this embodiment of the composition. Preferably, triethanolamine comprises from about 0.5% to about 3.0% of this embodiment of the composition. An optimum concentration of triethanolamine is about 1.25% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 7.0% of this embodiment of the composition. Preferably, cetyl alcohol comprises from about 2.0% to about 6.0% of this embodiment of the composition. An optimum concentration of cetyl alcohol is about 3.50% of this embodiment of the composition.

Stearic acid can comprise from about 0.50% to about 5.0% of this embodiment of the composition. Preferably, stearic acid comprises from about 1.0% to about 4.0% of this embodiment of the composition. An optimum concentration of stearic acid is about 2.50% of this embodiment of the composition.

Cod liver oil can comprise from about 1.0% to about 7.0% of this embodiment of the composition. Preferably, cod liver oil comprises from about 1.50% to about 5.0% of this embodiment of the composition. An optimum concentration of cod liver oil is about 2.0% of this embodiment of the composition.

Butylated hydroxytoluene can comprise from about 0.1% to about 1.0% of this embodiment of the composition. Preferably, butylated hydroxytoluene comprises from about 0.2% to about 0.8% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of the composition. An optimum concentration of propylparaben is about 0.25% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Still another embodiment of a composition according to the present invention is a composition comprising an oil-in-water emulsion comprising:
(1) allantoin; and
(2) an emulsifier system comprising:
  (a) sodium stearoyl lactylate;
  (b) sodium isostearoyl lactylate;
  (c) optionally, triethanolamine stearate;
  (d) optionally, at least one nonionic emulsifier selected from the group consisting of a nonionic emulsifier that is an ethoxylated ether or an ethoxylated ester whose carbon chain length ranges from 8 to 22 carbon atoms.

Sodium stearoyl lactylate is the sodium salt of the stearic acid ester of lactyl lactate. Sodium isostearoyl lactylate is the sodium salt of the isostearic acid ester of lactyl lactate.

In this embodiment of the composition, the composition further comprises an acid to adjust the pH to a range of from about 3.0 to about 6.0. Preferably, the pH is adjusted to a range of from about 5.0 to about 5.8. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of ethylene glycol, propylene glycol, glycerin, or butylene glycol. Preferably, the solvent component is propylene glycol.

This embodiment of the invention can further comprise an emollient component. The emollient component can comprise at least one emollient selected from the group consisting of lanolin oil, cetyl alcohol, and cod liver oil. Preferably, the emollient component comprises all of lanolin oil, cetyl alcohol, and cod liver oil.

This embodiment of the invention can further comprise a chelator component. Preferably, the chelator component is tetrasodium ethylenediaminetetraacetic acid.

This embodiment of the invention can further comprise a preservative component. The preservative component can comprise at least one preservative selected from the group consisting of methylparaben and propylparaben. Preferably, the preservative component comprises both methylparaben and propylparaben. As indicated above, other preservatives can be used.

This embodiment of the composition can also include an antioxidant. A preferred antioxidant is butylated hydroxytoluene. As indicated above, other antioxidants such as butylated hydroxyanisole can also be used.

This embodiment of the composition can further include fragrance as described above. The stability and function of the cream are not altered by the presence or absence of fragrance. As indicated above, it may be desirable to omit fragrance in some cases.

The following discussion describes ranges, preferred concentrations and optimum concentrations for preferred compositions according to this embodiment of the present invention when the pH is in the range of from about 5.0 to about 5.8.

Water can comprise from about 50.0% to about 90.0% of this embodiment of the composition. Preferably, water comprises from about 60.0% to about 80.0% of this embodiment of the composition. In one alternative, in which the optimum concentration of allantoin is about 1.50% of the composition, the optimum concentration of water is about 73.72% of the composition. In another alternative, in which the optimum concentration of allantoin is about 9.00% of the composition, the optimum concentration of water is about 66.22% of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

Citric acid can comprise from about 0.05% to about 0.50% of this embodiment of the composition. Preferably, citric acid comprises from about 0.10% to about 0.40% of this embodiment of the composition. An optimum concentration of citric acid is about 0.18% of this embodiment of the composition.

Sodium stearoyl lactylate can comprise from about 0.30% to about 3.0% of this embodiment of the composition. Preferably, sodium stearoyl lactylate comprises from about 0.50% to about 2.50% of this embodiment of the composition. An optimum concentration of sodium stearoyl acetylate is about 1.00% of this embodiment of the composition.

Sodium isostearoyl lactylate can comprise from about 0.05% to about 1.0% of this embodiment of the composition. Preferably, sodium isostearoyl lactylate comprises from about 0.10% to about 0.70% of this embodiment of the composition. An optimum concentration of sodium isostearoyl lactylate is about 0.25% of this embodiment of the composition.

Tetrasodium EDTA can comprise from about 0.05% to about 0.25% of this embodiment of the composition. Preferably, tetrasodium EDTA comprises from about 0.10% to about 0.20% of this embodiment of the composition. An optimum concentration of tetrasodium EDTA is about 0.15% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 1.0% to about 8.0% of this embodiment of the composition. Preferably, cetyl alcohol comprises from about 2.0% to about 7.0% of this embodiment of the composition. An optimum concentration of cetyl alcohol is about 3.80% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.0% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of the composition. An optimum concentration of propylparaben is about 0.25% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Still another embodiment of a composition according to the present invention is a composition comprising an oil-in-water emulsion comprising:

(1) allantoin; and (2) an emulsifier system comprising at least one polyethyleneglycol ether of cetearyl alcohol.

In polyethylene glycol ethers of cetearyl alcohol suitable for use in compositions according to the present invention, the number of ethylene glycol moieties can range from 6 to 40, e.g., $R(OCH_2CH_2)_{25}OH$ where R is $CH_3(CH_2)_{16-18}$. In one preferred embodiment of the present invention, the emulsifier system comprises both ceteareth-25 and ceteareth-6, i.e., polyethylene glycol ethers of cetearyl alcohol with 25 and 6 ethylene glycol units respectively.

In this embodiment of the composition, the composition further comprises an acid to adjust the pH to a range of from about 3.0 to about 6.0. Preferably, the pH is adjusted to a range of from about 5.0 to about 5.8. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of ethylene glycol, propylene glycol, glycerin, or butylene glycol. Preferably, the solvent component is propylene glycol.

This embodiment of the invention can further comprise a chelator component. Preferably, the chelator component is tetrasodium ethylenediaminetetraacetic acid.

This embodiment of the invention can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

This embodiment of the composition can also include an antioxidant. A preferred antioxidant is butylated hydroxytoluene. As indicated above, other antioxidants such as butylated hydroxyanisole can alternatively be used.

This embodiment of the invention can further comprise a preservative component. The preservative component can comprise at least one preservative selected from the group consisting of methylparaben, propylparaben, and diazolidinyl urea. Preferably, the preservative component comprises al of methylparaben, propylparaben, and diazolidinyl urea. As indicated above, other preservatives can alternatively be used.

This embodiment of the composition can further include fragrance as described above. The stability and function of the cream are not altered by the presence or absence of fragrance. As indicated above, it may be desirable to omit fragrance in some cases.

The following discussion describes ranges, preferred concentrations and optimum concentrations for preferred compositions according to this embodiment of the present invention when the pH is adjusted to a range of from about 5.0 to about 5.8.

Water can comprise from about 50.0% to about 90.0% of this embodiment of the composition. Preferably, water comprises from about 55.0% to about 75.0% of this embodiment of the composition. In one alternative, in which the optimum concentration of allantoin is about 1.50% of the composition, the optimum concentration of water is about 66.33% of the composition. In another alternative, in which the optimum concentration of allantoin is about 9.00% of the composition, the optimum concentration of water is about 58.83% of the composition.

Propylene glycol can comprise from about 2.0% to about 9.0% of this embodiment of the composition. Preferably, propylene glycol comprises from about 4.2% to about 7.0% of this embodiment of the composition. An optimum concentration of propylene glycol is about 5.70% of this embodiment of the composition.

Tetrasodium EDTA can comprise from about 0.05% to about 0.50% of this embodiment of the composition. Preferably, tetrasodium EDTA comprises from about 0.10% to about 0.30% of this embodiment of the composition. An optimum concentration of tetrasodium EDTA is about 0.15% of this embodiment of the composition.

Ceteareth-25 can comprise from about 0.50% to about 4.0% of this embodiment of the composition. Preferably, ceteareth-25 comprises from about 2.0% to about 3.5% of this embodiment of the composition. An optimum concentration of ceteareth-25 is about 2.60% of this embodiment of the composition.

Citric acid can comprise from about 0.04% to about 0.40% of this embodiment of the composition. Preferably, citric acid comprises from about 0.10% to about 0.30% of this embodiment of the composition. An optimum concentration of citric acid is about 0.12% of this embodiment of the composition.

Lanolin of can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 3.0% to about 10.0% of this embodiment of the composition. Preferably, cetyl alcohol comprises from about 3.5% to about 7.5% of this embodiment of the composition. An optimum concentration of cetyl alcohol is about 4.30% of this embodiment of the composition.

Stearyl alcohol can comprise from about 1.0% to about 5.0% of this embodiment of the composition. Preferably, stearyl alcohol comprises from about 2.0% to about 4.0% of this embodiment of the composition. An optimum concentration of stearyl alcohol is about 3.50% of this embodiment of the composition.

Ceteareth-6 can comprise from about 0.5% to about 4.0% of this embodiment of the composition. Preferably, ceteareth-6 comprises from about 1.0% to about 3.0% of this embodiment of the composition. An optimum concentration of ceteareth-6 is about 1.80% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Diazolidinyl urea can comprise from about 0.05% to about 0.50% of this embodiment of the composition. Preferably, diazolidinyl urea comprises from about 0.10% to about 0.30% of this embodiment of the composition. An optimum concentration of diazolidinyl urea is about 0.15% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Yet another embodiment of a composition according to the present invention is a composition comprising an oil-in-water emulsion comprising:

(1) allantoin; and
(2) an emulsifier system comprising:
 (a) a polyethylene glycol ester of stearic acid; and
 (b) glyceryl stearate.

Typically, the number of ethylene glycol moieties in the polyethylene glycol ester of stearic acid is from 25 to 100. Two preferred polyethylene glycol esters of stearic acid for use in this embodiment of compositions according to the present invention are PEG-40 stearate and PEG-100 stearate, with 40 and 100 ethylene glycol moieties respectively. A particularly preferred polyethylene glycol ester of stearic acid is PEG-100 stearate.

In this embodiment of the composition, the composition further comprises an acid to adjust the pH to a range of from about 3.0 to about 6.0. Preferably, the pH is adjusted to a range of from about 5.0 to about 5.8. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component is one or more of ethylene glycol, propylene glycol, glycerin, or butylene glycol. Preferably, the solvent component is propylene glycol.

This embodiment of the invention can further comprise a chelator component. Preferably, the chelator component is tetrasodium ethylenediaminetetraacetic acid.

This embodiment of the invention can further comprise an emollient component. The emollient component can comprise at least one emollient selected from the group consisting of lanolin oil, cetyl alcohol, stearyl alcohol, and cod liver oil. Preferably, the emollient component comprises al of lanolin oil, cetyl alcohol, stearyl alcohol, and cod liver oil.

This embodiment of the composition can also include an antioxidant. A preferred antioxidant is butylated hydroxytoluene. As indicated above, other antioxidants such as butylated hydroxyainsole can alternatively be used.

This embodiment of the invention can further comprise a preservative component. The preservative component can comprise at least one preservative selected from the group consisting of methylparaben, propylparaben, and diazolidinyl urea. Preferably, the preservative component comprises all of methylparaben, propylparaben, and diazolidinyl urea. As indicated above, other preservatives can alternatively be used.

This embodiment of the composition can further include fragrance as described above. The stability and function of the cream are not altered by the presence or absence of fragrance. As indicated above, it may be desirable to omit fragrance in some cases.

The following discussion describes ranges, preferred concentrations and optimum concentrations for preferred compositions according to this embodiment of the present invention when the pH is in the range of from about 5.0 to about 5.8.

Water can comprise from about 50.0% to about 90.0% of this embodiment of the composition. Preferably, water comprises from about 55.0% to about 80.0% of this embodiment of the composition. In one alternative in which the optimum concentration of allantoin is about 1.50% of the composition, the optimum concentration of water is about 67.86% of the composition. In another alternative, in which the optimum concentration of allantoin is about 9.00% of the composition, the optimum concentration of water is about 60.36% of the composition.

Propylene glycol can comprise from about 2.0% to about 9.0% of this embodiment of the composition. Preferably, propylene glycol comprises from about 4.30% to about 7.00% of this embodiment of the composition. An optimum concentration of propylene glycol is about 5.70% of this embodiment of the composition.

Tetrasodium EDTA can comprise from about 0.05% to about 0.50% of this embodiment of the composition. Preferably, tetrasodium EDTA comprises from about 0.10% to about 0.30% of this embodiment of the composition. An optimum concentration of tetrasodium EDTA is about 0.15% of this embodiment of the composition.

Citric acid can comprise from about 0.04% to about 0.40% of this embodiment of the composition. Preferably, citric acid comprises from about 0.10% to about 0.30% of this embodiment of the composition. An optimum concentration of citric acid is about 0.14% of this embodiment of the composition.

PEG-100 stearate can comprise from about 1.0% to about 5.0% of this embodiment of the composition. Preferably, PEG-100 stearate comprises from about 1.50% to about 3.00% of this embodiment of the composition. An optimum concentration of PEG-100 stearate is about 2.60% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil is about 10.60% of this embodiment of the composition.

Cetyl alcohol can comprise from about 2.0% to about 10.0% of this embodiment of the composition. Preferably, cetyl alcohol comprises from about 2.50% to about 7.50% of this embodiment of the composition. An optimum concentration of cetyl alcohol is about 3.00% of this embodiment of the composition.

Stearyl alcohol can comprise from about 1.0% to about 4.0% of this embodiment of the composition. Preferably, stearyl alcohol comprises from about 1.0% to about 3.5% of this embodiment of the composition. An optimum concentration of stearyl alcohol is about 2.50% of this embodiment of the composition.

Glyceryl stearate can comprise from about 1.0% to about 5.0% of this embodiment of the composition. Preferably, glyceryl stearate comprises from about 2.0% to about 4.0% of this embodiment of the composition. An optimum concentration of glyceryl stearate is about 2.50% of this embodiment of the composition.

Cod liver oil can comprise from about 1.0% to about 7.0% of this embodiment of the composition. Preferably, cod liver oil comprises from about 1.0% to about 4.0% of this embodiment of the composition. An optimum concentration of cod liver oil is about 2.00% of this embodiment of the composition.

Butylated hydroxytoluene can comprise from about 0.10% to about 1.0% of this embodiment of the composition. Preferably, butylated hydroxytoluene comprises from about 0.20% to about 0.80% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Diazolidinyl urea can comprise from about 0.05% to about 0.50% of this embodiment of the composition. Preferably, diazolidinyl urea comprises from about 0.10% to about 0.30% of this embodiment of the composition. An optimum concentration of diazolidinyl urea is about 0.20% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of this embodiment of the composition.

If present, fragrance can comprise from about 0.05% to about 0.50% of this embodiment of the composition. Preferably, fragrance comprises from about 0.10% to about 0.40% of this embodiment of the composition. An optimum concentration of fragrance is about 0.20% of this embodiment of the composition.

Yet another embodiment of a composition according to the present invention is a composition comprising an oil-in-water emulsion comprising:
(1) allantoin;
(2) a carbohydrate polymer; and
(3) an emulsifier system comprising:
  (a) an acidic wax; and
  (b) an anionic emulsifier that is substantially hydrophilic and is soluble in water.

Acidic waxes am those waxes having acidic groups that can be neutralized with alkaline materials such as hydroxides, alkoxides, unprotonated amines, and/or salts of strong bases and weak acids, such as sodium acetate. Upon neutralization, such waxes can act as emulsifiers or coemulsifiers. Preferred acidic waxes include beeswax, carnauba wax, candelilla wax, siliconyl beeswax, siliconyl carnauba wax, and synthetic acidic waxes. Examples of synthetic acidic waxes are syncrowaxes marketed by Croda, Inc. A particularly preferred acid wax is beeswax.

The carbohydrate polymer is typically selected from the group consisting of galactoarabinan, polygalactose, and polyarabinose. Preferably, the carbohydrate polymer is galactoarabinan.

The anionic emulsifier that is substantially hydrophilic and soluble in water can be selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate. A particularly preferred anionic emulsifier is sodium lauryl sulfate.

The pH of the composition is adjusted to a range of between about 3.0 and about 6.0, typically with an acid. Preferably, the pH is adjusted to a range of from about 5.0 to about 6.0. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of ethylene glycol, propylene glycol, glycerin, or butylene glycol. Preferably, the solvent component is propylene glycol.

This embodiment of the invention can further comprise a chelator component. Preferably, the chelator component is tetrasodium ethylenediaminetetraacetic acid.

This embodiment of the invention can further comprise an emollient component. The emollient component can comprise at least one emollient selected from the group consisting of lanolin oil, cetyl alcohol, stearyl alcohol, and cod liver oil. Preferably, the emollient component comprises all of lanolin oil, cetyl alcohol, stearyl alcohol, and cod liver oil.

This embodiment of the composition can also include an antioxidant. A preferred antioxidant is butylated hydroxytoluene. As indicated above, other antioxidants such as butylated hydroxyanisole (BHA) can also be used.

This embodiment of the invention can further comprise a preservative component. The preservative component can comprise one or more of methylparaben or propylparaben. Preferably, the preservative component comprises methylparaben and propylparaben. As indicated above, other preservatives can also be used.

This embodiment of the composition can further include fragrance as described above. The stability and function of the cream are not altered by the presence or absence of fragrance. As indicated above, it may be desirable to omit fragrance in some cases.

The following discussion describes ranges, preferred concentrations and optimum concentrations for preferred compositions according to this embodiment of the present invention when the pH is adjusted to a range of from about 5.0 to about 6.0.

Water can comprise from about 50.0% to about 90.0% of this embodiment of the composition. Preferably, water comprises from about 52.0% to about 80.0% of this embodiment of the composition. In an alternative in which the optimum concentration of allantoin is about 1.50% of the composition, the optimum concentration of water is about 61.65% of the composition. In another alternative, in which the optimum concentration of allantoin is about 9.00% of the composition, the optimum concentration of water is about 54.15% of the composition.

Propylene glycol can comprise from about 2.0% to about 9.0% of this embodiment of the composition. Preferably, propylene glycol comprises from about 4.0% to about 7.0% of this embodiment of the composition. An optimum concentration of propylene glycol is about 5.70% of this embodiment of the composition.

Sodium lauryl sulfate, as a 30% solution, can comprise from about 0.50% to about 5.0% of this embodiment of the composition. Preferably, sodium lauryl sulfate, as a 30% solution, comprises from about 1.0% to about 3.0% of this embodiment of the composition. An optimum concentration of sodium lauryl sulfate, as a 30% solution, is about 1.90% of this embodiment of the composition.

Tetrasodium EDTA can comprise from about 0.05% to about 0.30% of this embodiment of the composition. Preferably, tetrasodium EDTA comprises from about 0.10% to about 0.20% of this embodiment of the composition. An optimum concentration of tetrasodium EDTA is about 0.15% of this embodiment of the composition.

Galactoarabinan can comprise from about 1.0% to about 25.0% of this embodiment of the composition. Preferably, galactoarabinan comprises from about 3.0% to about 15.0% of this embodiment of the composition. An optimum concentration of galactoarabinan is about 5.00% of this embodiment of the composition.

Citric acid can comprise from about 0.05% to about 0.25% of this embodiment of the composition. Preferably, citric acid comprises from about 0.10% to about 0.20% of this embodiment of the composition. An optimum concentration of citric acid is about 0.15% of this embodiment of the composition.

Lanolin oil can comprise from about 5.0% to about 15.0% of this embodiment of the composition. Preferably, lanolin oil comprises from about 8.0% to about 12.0% of this embodiment of the composition. An optimum concentration of lanolin oil Is about 10.60% of this embodiment of the composition.

Cetyl alcohol can comprise from about 1.0% to about 8.0% of this embodiment of the composition. Preferably, cetyl alcohol comprises from about 2.0% to about 7.0% of this embodiment of the composition. An optimum concentration of cetyl alcohol is about 4.20% of this embodiment of the composition.

Stearyl alcohol can comprise from about 0.50% to about 6.0% of this embodiment of the composition. Preferably, stearyl alcohol comprises from about 1.0% to about 4.0% of this embodiment of the composition. An optimum concentration of stearyl alcohol is about 2.00% of this embodiment of the composition.

An acidic wax such as beeswax can comprise from about 0.50% to about 5.0% of this embodiment of the composition. Preferably, the acidic wax such as beeswax comprises from about 1.0% to about 3.0% of this embodiment of the composition. An optimum concentration of the acidic wax such as beeswax is about 1.90% of this embodiment of the composition.

Cod liver of can comprise from about 0.50% to about 15.0% of this embodiment of the composition. Preferably, cod river oil comprises from about 1.0% to about 10.0% of this embodiment of the composition. An optimum concentration of cod liver oils about 2.00% of this embodiment of the composition.

Butylated hydroxytoluene can comprise from about 0.1% to about 3.0% of this embodiment of the composition. Preferably, butylated hydroxytoluene comprises from about 0.25% to about 2.50% of this embodiment of the composition. An optimum concentration of butylated hydroxytoluene is about 0.50% of this embodiment of the composition.

Methylparaben can comprise from about 0.10% to about 0.50% of this embodiment of the composition. Preferably, methylparaben comprises from about 0.15% to about 0.40% of this embodiment of the composition. An optimum concentration of methylparaben is about 0.30% of this embodiment of the composition.

Propylparaben can comprise from about 0.10% to about 0.50% of this embodiment of the composition. Preferably, propylparaben comprises from about 0.15% to about 0.40% of this embodiment of the composition. An optimum concentration of propylparaben is about 0.25% of this embodiment of the composition.

Allantoin can comprise from about 0.50% to about 10.0% of this embodiment of the composition. In one alternative, a preferred concentration of allantoin is from about 1.0% to about 2.0% of this embodiment of the composition. In this alternative, an optimum concentration of allantoin is about 1.50% of this embodiment of the composition. In another alternative, an optimum concentration of allantoin is about 9.00% of this embodiment of the composition.

If present, fragrance can comprise from about 0.05% to about 0.50% of this embodiment of the composition. Preferably, if present, fragrance can comprise from about 0.10% to about 0.40% of this embodiment of the composition. An optimum concentration of fragrance is about 0.20% of this embodiment of the composition.

Yet another embodiment of a composition according to the present invention is a composition comprising an oil-in-water emulsion comprising:
 (1) allantoin in a concentration of at least about 2.5%;
 (2) an emulsifier system comprising:
  (a) an acidic wax; and
  (b) an anionic emulsifier that is substantially hydrophilic and is soluble in water.

The acidic waxes used are as described above. A particularly preferred acidic wax is beeswax.

The anionic emulsifier that is substantially hydrophilic and soluble in water can be selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, and sodium lauryl sulfate. A particularly preferred anionic emulsifier is sodium lauryl sulfate.

The pH of the composition is adjusted to a range of between about 3.0 and about 6.0, typically with an acid. The acid can be an inorganic or an organic acid as described above. Preferably, the acid is a weak organic acid. Most preferably, the acid is citric acid.

This embodiment can further comprise other ingredients. For example, this embodiment of the invention can further comprise a solvent component. Typically, the solvent component comprises at least one solvent selected from the group consisting of ethylene glycol, propylene glycol, glycerin, or butylene glycol. Preferably, the solvent component is propylene glycol.

This embodiment of the invention can further comprise a chelator component. Preferably, the chelator component is tetrasodium ethylenediaminetetraacetic acid.

This embodiment of the invention can further comprise an emollient component. The emollient component can comprise at least one emollient selected from the group consisting of lanolin oil, cetyl alcohol, and stearyl alcohol. Preferably, the emollient component comprises al of lanolin oil, cetyl alcohol, and stearyl alcohol.

This embodiment of the invention can further comprise a preservative component. The preservative component can comprise one or more of methylparaben or propylparaben. Preferably, the preservative component comprises methylparaben and propylparaben. As indicated above, other preservatives can also be used.

This embodiment of the composition can further include fragrance as described above. The stability and function of the cream are not altered by the presence or absence of fragrance. As indicated above, it may be desirable to omit fragrance in some cases.

The following discussion describes ranges, preferred concentrations and optimum concentrations for preferred compositions according to this embodiment of the present invention when the pH is adjusted to a range of from about 5.0 to about 6.0.

Water can comprise from about 50.0% to about 90.0% of this embodiment of the composition. An optimum concentration of water is about 58.98% of this embodiment of the composition Propylene glycol can comprise from about 2.0% to about 9.0% of this embodiment of the composition. An optimum concentration of propylene glycol is about 5.70% of this embodiment of the composition.

Sodium lauryl sulfate, as a 30% solution, can comprise from about 0.50% to about 5.0% of this embodiment of the composition. An optimum concentration of sodium lauryl sulfate, as a 30% solution, is about 3.00% of this embodiment of the composition.

Tetrasodium EDTA can comprise from about 0.05% to about 0.50% of this embodiment of the composition. An optimum concentration of tetrasodium EDTA is about 0.15% of this embodiment of the composition.

Citric acid can comprise from about 0.05% to about 0.50% of this embodiment of the composition. An optimum concentration of citric acid is about 0.12% of this embodiment of the composition.

Lanolin oil can comprise from about 5.0% to about 15.0% of this embodiment of the composition. An optimum concentration of lanolin oil is about 10.60% of this embodiment of the composition.

Cetyl alcohol can comprise from about 3.0% to about 10.0% of this embodiment of the composition. An optimum concentration of cetyl alcohol is about 4.20% of this embodiment of the composition.

Stearyl alcohol can comprise from about 1.0% to about 5.0% of this embodiment of the composition. An optimum concentration of stearyl alcohol is about 2.00% of this embodiment of the composition.

An acidic wax such as beeswax can comprise from about 0.50% to about 5.0% of this embodiment of the composition. An optimum concentration of the acidic wax such as beeswax is about 3.00% of this embodiment of the composition.

Methylparaben can comprise from about 0.10% to about 0.50% of this embodiment of the composition. An optimum concentration of methylparaben is about 0.30% of this embodiment of the composition.

Propylparaben can comprise from about 0.10% to about 0.50% of this embodiment of the composition. An optimum concentration of propylparaben is about 0.25% of this embodiment of the composition.

Allantoin can comprise from about 2.5% to about 10.0% of this embodiment of the composition. An optimum concentration of allantoin is about 9.00% of this embodiment of the composition.

If present, fragrance can comprise from about 0.05% to about 0.50% of this embodiment of the composition. An optimum concentration of fragrance is about 0.20% of this embodiment of the composition.

Examples of particularly preferred compositions according to the present invention are described below.

Compositions according to the present invention can contain other, optional ingredients. For example, compositions according to the present invention can contain lipid-soluble components such as, but not limited to, caprylic/capric triglycerides; steareth-2; steareth-21; polyglyceryl-3 beeswax; a branched-carboxylic acid ester of a branched-chain alcohol selected from the group consisting of isononyl isononanoate, isodecyl isononanoate, isooctyl isononanoate, isononyl isooctanoate, isodecyl isooctanonoate, isooctyl isooctanoate, isononyl isodecanoate, isooctyl isodecanoate, and isodecyl isodecanoate; an acrylates/$C_{10}$-$C_{30}$ alkyl acrylates crosspolymer methylgluceth-20; a glyceryl ester of a long-chain fatty acid selected from the group consisting of glyceryl monostearate, glyceryl monopalmitate, and glyceryl monoarachidate; hydrogenated vegetable oil; squalane; $C_{12}$-$C_{15}$ alkyl benzoates; di-$C_{12}$-$C_{15}$ alkyl fumarate; cholesterol; lanolin alcohol; octyldodecanol; isostearic acid; a branched-chain neopentanoate selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate; an arachidyl ester of a short-chain carboxylic acid selected from the group consisting of arachidyl propionate, arachidyl acetate, arachidyl butyrate, and arachidyl isobutyrate; a long-chain fatty acid ester of a medium-chain alcohol selected from the group consisting of octyl palmitate, octyl myristate, octyl stearate, heptyl palmitate, heptyl myristate, heptyl stearate, nonyl palmitate, nonyl myristate, and nonyl stearate; jojoba oil; a myristyl ester of a long-chain fatty acid selected from the group consisting of myristyl myristate, myristyl laurate, and myristyl palmitate; bisabolol; hydrogenated jojoba oil; jojoba esters; methylgluceth-20 sesquistearate; PPG-14 butyl ether; PPG-15 stearyl ether; PPG-1-isoceteth-3-acetate; laureth-2-benzoate; diisostearyl dimer dilinoleate; a long-chain cis-monounsaturated fatty acid ester of a medium-chain alcohol; a medium-chain saturated carboxylic acid ester of a long-chain alcohol; hydrogenated soy glycerides; a long-chain fatty acid ester of cetyl alcohol selected from the group consisting of cetyl palmitate, cetyl stearate, and cetyl myristate; palm kernel oil; palm oil; and an arachidyl ester selected from the group consisting of arachidyl acetate, arachidyl propionate, arachidyl butyrate, and arachidyl isobutyrate.

In addition, the composition can further comprise other ingredients that are generally used in the cosmetic art and in the art of over-the-counter skin preparations. These ingredients include, but are not limited to: (1) other plant extracts, such as horsetail extract, horse chestnut extract, rose extract, or lavender extract; (2) a short-chain carboxylic acid ester of tocopherol selected from the group consisting of tocopheryl acetate, tocopheryl propionate, tocopheryl butyrate, and tocopheryl isobutyrate; (3) a long-chain fatty acid ester of ascorbic acid selected from the group consisting of ascorbyl myristate, ascorbyl palmitate, and ascorbyl stearate; (4) a long-chain fatty acid ester of retinol or a retinol derivative or analogue wherein the acyl moiety of the ester is selected from the group consisting of myristic acid, palmitic acid, and stearic acid; and (5), a sunscreen, which can be at least one compound selected from the group consisting of octyl methoxycinnamate, p-aminobenzoic acid, ethyl p-aminobenzoate, isobutyl p-aminobenzoate, glyceryl p-aminobenzoate, dimethylaminobenzoic acid, methyl anthranilate, menthyl anthranilate, phenyl anthranilate, benzyl anthranilate, phenylethyl anthranilate, linalyl anthranilate, terpinyl anthranilate, cyclohexenyl anthranilate, amyl salicylate, phenyl salicylate, benzyl salicylate, menthyl salicylate, glyceryl salicylate, dipropyleneglycol salicylate, methyl cinnamate, benzyl cinnamate, α-phenyl cinnamonitrile, butyl cinnamoylpyruvate, umbelliferone, methylacetoumbelliferone, esculetin, methylesculetin, daphnetin, esculin, daphnin, diphenylbutadiene, stilbene, dibenzalacetone, benzalacetophenone, sodium 2-naphthol-3,6-disulfonate, sodium 2-naphthol-6,8-disulfonate, dihydroxynaphthoic acid, salts of dihydroxynaphthoic acid, o-hydroxybiphenyldisulfonates, p-hydroxybiphenyldisulfonates, 7-hydroxycoumarin, 7-methylcoumarin, 3-phenylcoumarin, 2-acetyl-3-bromoindazole, phenylbenzoxazole, methylnaphthoxazole, arylbenzothiazoles, quinine bisulfate, quinine sulfate, quinine chloride, quinine oleate, quinine tannate, 8-hydroxyquinoline salts, 2-phenylquinoline, hydroxy-substituted benzophenones, methoxy-substituted benzophenones, uric acid, vilouric acid, tannic acid, tannic acid hexaethylether, hydroquinone, oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyldibenzoylmethane.

Other ingredients can also optionally be included, such as colorants, pigments, opacifiers, and the like.

The composition is prepared by standard mixing techniques, such as are conventional in the cosmetic art and in the art of over-the-counter drug formulation for blending lipid-soluble components and water-soluble components. These mixing techniques include both manual and mechanical mixing, and include homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients. The composition can be mixed in two or more batches, such as one batch containing lipid-soluble ingredients and another batch containing water-soluble ingredients, and the batches can then be mixed at the final stage of preparation.

The batches to be used are shown in Tables 1-20.

Compositions according to the present invention can be formulated for the treatment of skin diseases and conditions. Among the skin diseases and conditions for which compositions according to the present invention can be formulated are epidermolysis bullosa, decubitus ulcers, pressure ulcers, diabetic ulcers, and milia. Compositions according to the present invention can be formulated for treatment of other skin diseases and conditions. The details of the composition can be varied according to the particular condition to be treated. For example, greater or lesser degrees of oil or lipid-soluble components can be included, and, in the case of compositions intended to be used on patients who may undergo allergic reactions, compounds that often generate allergic reactions, such as fragrance and coloring, can be excluded. Such details can readily be ascertained by one of ordinary skill in the art.

The invention is illustrated by the following Examples. These Examples are for illustrative purposes only and are not intended to limit the invention.

Example 1

Preparation of Skin Protectant Over-the-Counter Cream with pH of 7.4

Prior Art Example

A skin protectant over-the-counter (OTC) cream was prepared in accordance with the formulation of Table 1.

TABLE 1

COMPOSITION OF ALLANTOIN-CONTAINING SKIN CREAM WITH pH OF 7.4

| INGREDIENT | RANGE | PREFERRED | OPTIMUM |
| --- | --- | --- | --- |
| Part A | | | |
| Water | 50.0-90.0 | 55.0-75.0 | 66.20 |
| Sodium Lauryl Sulfate (30%) | 0.50-2.50 | 1.00-2.50 | 1.90 |
| Propylene Glycol | 2.0-9.0 | 3.0-6.0 | 5.30 |
| Tetrasodium EDTA | 0.05-0.50 | 0.10-0.30 | 0.15 |
| Part B | | | |
| Lanolin Oil | 5.0-15.0 | 8.0-12.0 | 10.60 |
| Cetyl Alcohol | 3.0-10.0 | 3.5-7.5 | 6.80 |

TABLE 1-continued

COMPOSITION OF ALLANTOIN-CONTAINING
SKIN CREAM WITH pH OF 7.4

| INGREDIENT | RANGE | PREFERRED | OPTIMUM |
|---|---|---|---|
| Stearyl Alcohol | 1.0-5.0 | 1.0-3.0 | 2.00 |
| Beeswax | 0.50-2.50 | 1.0-2.5 | 1.90 |
| Cod Liver Oil | 1.0-7.0 | 1.0-4.0 | 2.00 |
| BHT | 0.10-1.00 | 0.20-0.80 | 0.50 |
| Part C | | | |
| St. John's Wort Extract | 0.05-0.50 | 0.05-0.15 | 0.10 |
| Witch Hazel Extract | 0.05-0.50 | 0.05-0.15 | 0.10 |
| *Chamomile* Extract | 0.05-0.50 | 0.05-0.15 | 0.10 |
| *Arnica* Extract | 0.05-0.50 | 0.05-0.15 | 0.10 |
| Methylparaben | 0.10-0.50 | 0.15-0.40 | 0.30 |
| Propylparaben | 0.10-0.50 | 0.10-0.30 | 0.25 |
| Allantoin | 0.50-2.00 | 0.50-2.00 | 1.50 |
| Fragrance | 0.05-0.50 | 0.10-0.30 | 0.20 |

The Part A ingredients were combined and heated to 175° F. with mixing. The Part B ingredients were combined and heated to 175° F. with mixing. The Part B mixture was then added to the Part A mixture with mixing. The resulting mixture was then cooled to 120° F. with continued mixing. The Part C ingredients were then added with mixing. The final emulsion was allowed to cool with continued mixing. The resulting cream had a pH of 7.4. Samples of the cream prepared from Example 1 were used for accelerated aging stability studies and analyzed for their allantoin concentration after a period of time at 40° C. The results are shown in Table 2.

As can be seen from Table 2, the allantoin in the cream from Example 1 undergoes degradation and would not meet the specifications required for an OTC drug.

TABLE 2

STABILITY OF ALLANTOIN IN SKIN CREAM COMPOSITION
OF EXAMPLE 1 WITH STORAGE AT 40° C.

| Days at 40° C. | Weight % Allantoin |
|---|---|
| 0 | 1.5 |
| 30 | 1.4 |
| 60 | 1.3 |
| 90 | 1.2 |

Example 2

Preparation of a Cream Containing Allantoin with Lower pH

An OTC skin cream containing allantoin was prepared using the ingredients in Table 3 to provide a cream with a lower pH.

TABLE 3

COMPOSITION OF ALLANTOIN-CONTAINING
SKIN CREAM WITH pH OF 5.3

| INGREDIENT | RANGE | PREFERRED | OPTIMUM |
|---|---|---|---|
| Part A | | | |
| Water | 50.0-90.0 | 55.0-75.0 | 68.68 |
| Sodium Lauryl Sulfate (30%) | 0.50-2.50 | 1.00-2.50 | 1.90 |
| Propylene Glycol | 2.0-9.0 | 3.0-6.0 | 5.30 |

TABLE 3-continued

COMPOSITION OF ALLANTOIN-CONTAINING
SKIN CREAM WITH pH OF 5.3

| INGREDIENT | RANGE | PREFERRED | OPTIMUM |
|---|---|---|---|
| Tetrasodium EDTA | 0.05-0.50 | 0.10-0.30 | 0.15 |
| Citric Acid | 0.05-0.50 | 0.08-0.35 | 0.12 |
| Part B | | | |
| Lanolin Oil | 5.0-15.0 | 8.0-12.0 | 10.60 |
| Cetyl Alcohol | 3.0-10.0 | 3.5-7.5 | 4.20 |
| Stearyl Alcohol | 1.0-5.0 | 1.0-3.0 | 2.00 |
| Beeswax | 0.50-2.50 | 1.0-2.5 | 1.90 |
| Cod Liver Oil | 1.0-7.0 | 1.0-4.0 | 2.00 |
| BHT | 0.10-1.00 | 0.20-0.80 | 0.50 |
| Part C | | | |
| St. John's Wort Extract | 0.05-0.50 | 0.05-0.15 | 0.10 |
| Witch Hazel Extract | 0.05-0.50 | 0.05-0.15 | 0.10 |
| *Chamomile* Extract | 0.05-0.50 | 0.05-0.15 | 0.10 |
| *Arnica* Extract | 0.05-0.50 | 0.05-0.15 | 0.10 |
| Methylparaben | 0.10-0.50 | 0.15-0.40 | 0.30 |
| Propylparaben | 0.10-0.50 | 0.10-0.30 | 0.25 |
| Allantoin | 0.50-10.0 | 0.50-2.00 | 1.50 |
| Fragrance | 0.05-0.50 | 0.10-0.30 | 0.20 |

The Part A ingredients were combined and heated to 175° F. with mixing. The Part B ingredients were combined and heated to 175° F. with mixing. The Part B mixture was added to the Part A mixture with mixing. The resulting mixture was then cooled to 120° F. with mixing at which time the Part C ingredients were added with mixing. The final emulsion was allowed to cool with continue mixing. The resulting cream had a pH of 5.3.

The citric acid is added to adjust the pH. Another acidic wax can be used to replace the beeswax as described above.

It was found that a similar cream was produced if Part B was added to Part A or Part A was added to Part B. However, the cream has a better appearance if the oil phase and water phase are homogenized under high shear after the two phases are added to one another.

Samples of the cream of this example were used for accelerated aging stability studies and analyzed for their allantoin concentration. The results are shown in Table 4. As can be seen from Table 4, the allantoin is stable over time in a cream with a pH of 5.3.

TABLE 4

STABILITY OF ALLANTOIN IN SKIN CREAM
COMPOSITION OF EXAMPLE 2 WITH STORAGE AT 40° C.

| Days at 40° C. | Weight % Allantoin |
|---|---|
| 0 | 1.4 |
| 30 | 1.4 |
| 60 | 1.4 |
| 90 | 1.4 |

Example 3

Preparation of Allantoin-Containing Skin Cream with Ionic Emulsifiers

An allantoin-containing skin cream with ionic emulsifiers is prepared according to Table 5. The preparation follows the method used in Example 2, with the ingredients in each of Part A, Part B, and Part C being combined separately and then Part B being added to Part A, with Part C then being added to the combination of Part A and Part B. The pH is adjusted to a value in a range of from about 5.0 to about 5.8 by neutralizing the stearic acid with enough triethanolamine to reach this pH. Other bases can be used instead of triethanolamine.

TABLE 5

ALLANTOIN-CONTAINING SKIN CREAM WITH IONIC EMULSIFIERS

| INGREDIENT | RANGE | PREFERRED | OPTIMUM |
|---|---|---|---|
| Part A | | | |
| Water | 50.0-90.0 | 60.0-85.0 | 71.70 |
| Propylene Glycol | 2.0-9.0 | 4.0-7.0 | 5.70 |
| Triethanolamine (99%) | 0.20-4.0 | 0.50-3.0 | 1.25 |
| Part B | | | |
| Lanolin Oil | 5.0-15.0 | 8.0-12.0 | 10.60 |
| Cetyl Alcohol | 1.0-7.0 | 2.0-6.0 | 3.50 |
| Stearic Acid | 0.50-5.0 | 1.0-4.0 | 2.50 |
| Cod Liver Oil | 1.0-7.0 | 1.5-5.0 | 2.00 |
| Butylated Hydroxytoluene | 0.10-1.0 | 0.20-0.80 | 0.50 |
| Part C | | | |
| Methylparaben | 0.10-0.50 | 0.15-0.40 | 0.30 |
| Propylparaben | 0.10-0.50 | 0.15-0.40 | 0.25 |
| Allantoin | 0.50-10.0 | 1.0-2.0 | 1.50 |
| Fragrance | 0.05-0.50 | 0.10-0.40 | 0.20 |

Example 4

Preparation of Allantoin-Containing Skin Cream with Lactylate Emulsifiers

An allantoin-containing skin cream with the emulsifiers sodium stearoyl lactylate and sodium isostearoyl lactylate is prepared according to Table 6. The preparation follows the method used in Example 3. The pH is adjusted by the addition of the appropriate quantity of citric acid.

TABLE 6

ALLANTOIN-CONTAINING SKIN CREAM WITH LACTYLATE EMULSIFIERS

| INGREDIENT | RANGE | PREFERRED | OPTIMUM |
|---|---|---|---|
| Part A | | | |
| Water | 50.0-90.0 | 60.0-80.0 | 73.42 |
| Propylene Glycol | 2.0-9.0 | 4.0-7.0 | 5.70 |
| Citric Acid | 0.05-0.50 | 0.10-0.40 | 0.18 |
| Sodium Stearoyl Lactylate | 0.30-3.0 | 0.50-2.50 | 1.00 |
| Sodium Isostearoyl Lactylate | 0.05-1.0 | 0.10-0.70 | 0.25 |
| Tetrasodium EDTA | 0.05-0.25 | 0.10-0.20 | 0.15 |
| Part B | | | |
| Lanolin OH | 5.0-15.0 | 8.0-12.0 | 10.60 |
| Cetyl Alcohol | 1.0-8.0 | 2.0-7.0 | 3.80 |
| Cod Liver Oil | 1.0-7.0 | 1.0-4.0 | 2.00 |
| Butylated Hydroxytoluene | 0.10-1.0 | 0.20-0.80 | 0.50 |
| Part C | | | |
| Methylparaben | 0.10-0.50 | 0.15-0.40 | 0.30 |
| Propylparaben | 0.10-0.50 | 0.15-0.40 | 0.25 |
| Allantoin | 0.50-10.0 | 1.0-2.0 | 1.50 |
| Fragrance | 0.05-0.50 | 0.10-0.40 | 0.20 |

Example 5

Preparation of Allantoin-Containing Skin Cream with Carboxypolymethylene Polymer An allantoin-containing skin cream with carboxypolymethylene polymer is prepared according to Table 7. The preparation follows the method used in Example 3, except that the triethanolamine (Part D) is added last, after the combining of Parts A, B, and C, to avoid thickening of the emulsion. The triethanolamine is added to adjust the pH.

TABLE 7

ALLANTOIN-CONTAINING SKIN CREAM WITH CARBOXYPOLYMETHYLENE POLYMER

| INGREDIENT | RANGE | PREFERRED | OPTIMUM |
|---|---|---|---|
| Part A | | | |
| Water | 50.0-90.0 | 60.0-80.0 | 73.55 |
| Carboxypolymethylene Polymer | 0.40-3.0 | 0.50-2.0 | 1.00 |
| Propylene Glycol | 2.0-9.0 | 4.0-7.0 | 5.70 |
| Part B | | | |
| Lanolin Oil | 5.0-15.0 | 8.0-12.0 | 10.00 |
| Cetyl Alcohol | 1.0-8.0 | 2.0-7.0 | 3.00 |
| Cod Liver Oil | 1.0-7.0 | 1.0-4.0 | 2.00 |
| Butylated Hydroxytoluene | 0.10-1.0 | 0.20-0.80 | 0.50 |
| Part C | | | |
| Methylparaben | 0.10-0.50 | 0.15-0.40 | 0.30 |
| Propylparaben | 0.10-0.50 | 0.15-0.40 | 0.25 |
| Allantoin | 0.50-10.0 | 1.0-2.0 | 1.50 |
| Fragrance | 0.05-0.50 | 0.10-0.40 | 0.20 |
| Part D | | | |
| Triethanolamine (99%) | 0.05-3.0 | 0.20-2.0 | 0.80 |

Example 6

Preparation of Allantoin-Containing Skin Cream with Polyethylene Glycol Ethers of Cetearyl Alcohol An allantoin-containing skin cream with polyethylene glycol ethers of cetearyl alcohol is prepared according to Table 8. The preparation follows the method used in Example 3. The citric acid is added to adjust the pH.

TABLE 8

ALLANTOIN-CONTAINING SKIN CREAM WITH POLYETHYLENE GLYCOL ETHERS OF CETEARYL ALCOHOL

| INGREDIENT | RANGE | PREFERRED | OPTIMUM |
|---|---|---|---|
| Part A | | | |
| Water | 50.0-90.0 | 55.0-75.0 | 66.33 |
| Propylene Glycol | 2.0-9.0 | 4.0-7.0 | 5.70 |
| Tetrasodium EDTA | 0.05-0.50 | 0.10-0.30 | 0.15 |
| Ceteareth-25 | 0.50-4.0 | 2.00-3.50 | 2.60 |
| Citric Acid | 0.04-0.40 | 0.10-0.30 | 0.12 |
| Part B | | | |
| Lanolin Oil | 5.0-15.0 | 8.0-12.0 | 10.60 |
| Cetyl Alcohol | 3.0-10.0 | 3.5-7.5 | 4.30 |
| Stearyl Alcohol | 1.0-5.0 | 2.0-4.0 | 3.50 |
| Ceteareth-6 | 0.50-4.0 | 1.0-3.0 | 1.80 |
| Cod Liver Oil | 1.0-7.0 | 1.0-4.0 | 2.00 |
| Butylated Hydroxytoluene | 0.10-1.0 | 0.20-0.80 | 0.50 |

TABLE 8-continued

ALLANTOIN-CONTAINING SKIN CREAM WITH
POLYETHYLENE GLYCOL ETHERS OF CETEARYL ALCOHOL

| INGREDIENT | RANGE | PREFERRED | OPTIMUM |
|---|---|---|---|
| Part C | | | |
| Methylparaben | 0.10-0.50 | 0.15-0.40 | 0.30 |
| Propylparaben | 0.10-0.50 | 0.15-0.40 | 0.25 |
| Diazolidinyl Urea | 0.05-0.50 | 0.10-0.30 | 0.15 |
| Allantoin | 0.50-10.0 | 1.0-2.0 | 1.50 |
| Fragrance | 0.05-0.50 | 0.10-0.30 | 0.20 |

Example 7

Preparation of Allantoin-Containing Skin Cream with Polyethylene Glycol Ester of Stearic Acid and Glyceryl Stearate An allantoin-containing skin cream with a polyethylene glycol ester of stearic acid and glyceryl stearate is prepared according to Table 9. The preparation follows the method used in Example 3. The citric acid is added to adjust the pH.

TABLE 9

ALLANTOIN-CONTAINING SKIN CREAM WITH
POLYETHYLENE GLYCOL ESTER OF STEARIC ACID
AND GLYCERYL STEARATE

| INGREDIENT | RANGE | PREFERRED | OPTIMUM |
|---|---|---|---|
| Part A | | | |
| Water | 50.0-90.0 | 55.0-80.0 | 67.86 |
| Propylene Glycol | 2.0-9.0 | 4.3-7.0 | 5.70 |
| Tetrasodium EDTA | 0.05-0.50 | 0.10-0.30 | 0.15 |
| Citric Add | 0.04-0.40 | 0.10-0.30 | 0.14 |
| PEG-100 Stearate | 1.0-5.0 | 1.5-3.0 | 2.60 |
| Part B | | | |
| Lanolin Oil | 5.0-15.0 | 2.0-12.0 | 10.60 |
| Cetyl Alcohol | 3.0-10.0 | 2.5-7.5 | 3.0 |
| Stearyl Alcohol | 1.0-4.0 | 1.0-3.5 | 2.50 |
| Glyceryl Stearate | 1.0-5.0 | 2.0-4.0 | 2.50 |
| Cod Liver Oil | 1.0-7.0 | 1.0-4.0 | 2.00 |
| Butylated Hydroxytoluene | 0.10-1.0 | 0.20-0.80 | 0.50 |
| Part C | | | |
| Methylparaben | 0.10-0.50 | 0.15-0.40 | 0.30 |
| Propylparaben | 0.10-0.50 | 0.15-0.40 | 0.25 |
| Diazolidinyl Urea | 0.05-0.50 | 0.10-0.30 | 0.20 |
| Allantoin | 0.50-10.0 | 1.0-2.0 | 1.50 |
| Fragrance | 0.05-0.50 | 0.10-0.40 | 0.20 |

Example 8

Preparation of Allantoin-Containing Skin Cram with Carboxypolymethylene Polymer and Polyethylene Glycol Ester of Stearic Acid An allantoin-containing skin cream with a carboxypolymethylene polymer and a polyethylene glycol ester of stearic acid is prepared according to Table 10. The preparation follows the method used in Example 5, with the triethanolamine (Part D) being added last. The triethanolamine is added to adjust the pH.

TABLE 10

ALLANTOIN-CONTAINING SKIN CREAM WITH
A CARBOXYPOLYMETHYLENE POLYMER AND A
POLYETHYLENE GLYCOL ESTER OF STEARIC ACID

| INGREDIENT | RANGE | PREFERRED | OPTIMUM |
|---|---|---|---|
| Part A | | | |
| Water | 50.0-90.0 | 60.0-85.0 | 69.95 |
| Carboxypolymethylene Polymer | 0.30-3.0 | 0.50-2.0 | 0.85 |
| Propylene Glycol | 2.0-9.0 | 4.0-7.0 | 5.70 |
| PEG-100 Stearate | 0.25-2.5 | 0.50-2.0 | 1.50 |
| Part B | | | |
| Lanolin Oil | 5.0-15.0 | 8.0-12.0 | 10.60 |
| Cetyl Alcohol | 1.0-8.0 | 2.0-7.0 | 4.20 |
| Stearyl Alcohol | 0.50-6.0 | 0.75-5.0 | 1.50 |
| Cod Liver Oil | 1.0-7.0 | 1.0-4.0 | 2.00 |
| Butylated Hydroxytoluene | 0.10-1.0 | 0.20-0.80 | 0.50 |
| Part C | | | |
| Methylparaben | 0.10-0.50 | 0.15-0.40 | 0.30 |
| Propylparaben | 0.10-0.50 | 0.15-0.40 | 0.25 |
| Diazolidinyl Urea | 0.05-0.25 | 0.10-0.20 | 0.15 |
| Allantoin | 0.50-10.0 | 1.0-2.0 | 1.50 |
| Fragrance | 0.05-0.50 | 0.10-0.40 | 0.20 |
| Part D | | | |
| Triethanolamine (99%) | 0.05-3.0 | 0.20-2.0 | 0.80 |

Example 9

Preparation of allantoin-Containing Skin Cream with Galactoarabinan, Sodium Lauryl Sulfate, and Beeswax An allantoin-containing skin cream with galactoarabinan, sodium lauryl sulfate, and beeswax is prepared according to Table 11. The preparation follows the method used in Example 3. The citric acid is used to adjust the pH. Another acidic wax can substitute for beeswax.

TABLE 11

ALLANTOIN-CONTAINING SKIN CREAM WITH
GALACTOARABINAN, SODIUM LAURYL SULFATE
AND BEESWAX

| INGREDIENT | RANGE | PREFERRED | OPTIMUM |
|---|---|---|---|
| Part A | | | |
| Water | 50.0-90.0 | 60.0-80.0 | 61.65 |
| Propylene Glycol | 2.0-9.0 | 4.0-7.0 | 5.70 |
| Sodium Lauryl Sulfate (30%) | 0.50-5.0 | 1.0-3.0 | 1.90 |
| Tetrasodium EDTA | 0.05-0.30 | 0.10-0.20 | 0.15 |
| Galactoarabinan | 1.0-25.0 | 3.0-15.0 | 5.00 |
| Citric Acid | 0.05-0.25 | 0.10-0.20 | 0.15 |
| Part B | | | |
| Lanolin Oil | 5.0-15.0 | 8.0-12.0 | 10.60 |
| Cetyl Alcohol | 1.0-8.0 | 2.0-7.0 | 4.20 |
| Stearyl Alcohol | 0.50-6.0 | 1.0-4.0 | 2.00 |
| Beeswax | 0.50-5.0 | 1.0-3.0 | 1.90 |
| Cod Liver Oil | 0.50-15.0 | 1.0-10.0 | 2.00 |
| Butylated Hydroxytoluene | 0.10-3.0 | 0.25-2.5 | 0.50 |
| Part C | | | |
| Methylparaben | 0.10-0.50 | 0.15-0.40 | 0.30 |
| Propylparaben | 0.10-0.50 | 0.15-0.40 | 0.25 |
| Allantoin | 0.50-10.0 | 1.0-2.0 | 1.50 |
| Fragrance | 0.05-0.50 | 0.10-0.40 | 0.20 |

Example 10

Preparation of a Cream Containing Allantoin with pH of 5.3 with High Allantoin Concentration An OTC skin cream containing allantoin is prepared using the Ingredients in Table 12 to provide a cream with a lower pH with an allantoin concentration of about 9.00%. The skin cream is prepared according to the method of Example 2.

TABLE 12

COMPOSITION OF ALLANTOIN-CONTAINING SKIN CREAM WITH pH OF 5.3 WITH HIGH ALLANTOIN CONCENTRATION

| INGREDIENT | RANGE | OPTIMUM |
|---|---|---|
| Part A | | |
| Water | 50.0-90.0 | 61.38 |
| Sodium Lauryl Sulfate (30%) | 0.50-2.50 | 1.90 |
| Propylene Glycol | 2.0-9.0 | 5.30 |
| Tetrasodium EDTA | 0.05-0.50 | 0.15 |
| Citric Acid | 0.05-0.50 | 0.12 |
| Part B | | |
| Lanolin Oil | 5.0-15.0 | 10.60 |
| Cetyl Alcohol | 3.0-10.0 | 4.20 |
| Stearyl Alcohol | 1.0-5.0 | 2.00 |
| Beeswax | 0.50-2.50 | 1.90 |
| Cod Liver Oil | 1.0-7.0 | 2.00 |
| BHT | 0.10-1.00 | 0.50 |
| Part C | | |
| St. John's Wort Extract | 0.05-0.50 | 0.10 |
| Witch Hazel Extract | 0.05-0.50 | 0.10 |
| Chamomile Extract | 0.05-0.50 | 0.10 |
| Arnica Extract | 0.05-0.50 | 0.10 |
| Methylparaben | 0.10-0.50 | 0.30 |
| Propylparaben | 0.10-0.50 | 0.25 |
| Allantoin | 0.50-10.00 | 9.00 |
| Fragrance | 0.05-0.50 | 0.20 |

Example 11

Preparation of Allantoin-Containing Skin Cream with Ionic Emulsifiers with High Allantoin Concentration An OTC skin cream containing allantoin is prepared using the ingredients in Table 13 to provide a cream with an allantoin concentration of about 9.00% using ionic emulsifiers. The skin cream is prepared according to the method of Example 3. The pH is adjusted to a value in a range of from about 5.0 to about 5.8 by neutralizing the stearic acid with enough triethanolamine to reach this pH. Other bases can be used instead of triethanolamine.

TABLE 13

ALLANTOIN-CONTAINING SKIN CREAM WITH IONIC EMULSIFIERS WITH HIGH ALLANTOIN CONCENTRATION

| INGREDIENT | RANGE | OPTIMUM |
|---|---|---|
| Part A | | |
| Water | 50.0-90.0 | 64.20 |
| Propylene Glycol | 2.0-9.0 | 5.70 |
| Triethanolamine (99%) | 0.20-4.0 | 1.25 |

TABLE 13-continued

ALLANTOIN-CONTAINING SKIN CREAM WITH IONIC EMULSIFIERS WITH HIGH ALLANTOIN CONCENTRATION

| INGREDIENT | RANGE | OPTIMUM |
|---|---|---|
| Part B | | |
| Lanolin Oil | 5.0-15.0 | 10.60 |
| Cetyl Alcohol | 1.0-7.0 | 3.50 |
| Stearic Acid | 0.50-5.0 | 2.50 |
| Cod Liver Oil | 1.0-7.0 | 2.00 |
| Butylated Hydroxytoluene | 0.10-1.0 | 0.50 |
| Part C | | |
| Methylparaben | 0.10-0.50 | 0.30 |
| Propylparaben | 0.10-0.50 | 0.25 |
| Allantoin | 0.50-10.0 | 9.00 |
| Fragrance | 0.05-0.50 | 0.20 |

Example 12

Preparation of a Cream Containing Allantoin with Lactylate Emulsifiers with High Allantoin Concentration An OTC skin cream containing allantoin is prepared using the ingredients in Table 14 to provide a cream with an allantoin concentration of about 9.00% using lactylate emulsifiers. The skin cream is prepared according to the method of Example 4. The pH is adjusted by the addition of the appropriate quantity of citric acid.

TABLE 14

ALLANTOIN-CONTAINING SKIN CREAM WITH LACTYLATE EMULSIFIERS WITH HIGH ALLANTOIN CONCENTRATION

| INGREDIENT | RANGE | OPTIMUM |
|---|---|---|
| Part A | | |
| Water | 50.0-90.0 | 65.92 |
| Propylene Glycol | 2.0-9.0 | 5.70 |
| Citric Acid | 0.05-0.50 | 0.18 |
| Sodium Stearoyl Lactylate | 0.30-3.0 | 1.00 |
| Sodium Isostearoyl Lactylate | 0.05-1.0 | 0.25 |
| Tetrasodium EDTA | 0.05-0.25 | 0.15 |
| Part B | | |
| Lanolin Oil | 5.0-15.0 | 10.60 |
| Cetyl Alcohol | 1.0-8.0 | 3.80 |
| Cod Liver Oil | 1.0-7.0 | 2.00 |
| Butylated Hydroxytoluene | 0.10-1.0 | 0.50 |
| Part C | | |
| Methylparaben | 0.10-0.50 | 0.30 |
| Propylparaben | 0.10-0.50 | 0.25 |
| Allantoin | 0.50-10.0 | 9.00 |
| Fragrance | 0.05-0.50 | 0.20 |

Example 13

Preparation of a Cream Containing Allantoin with Carboxypolymethylene Polymer with High Allantoin Concentration An OTC skin cream containing allantoin is prepared using the ingredients in Table 15 to provide a cream with an allantoin concentration of about 9.00% with a carboxypolymethylene polymer. The skin cream is prepared according to the method of Example 5. Triethanolamine is added to adjust the pH.

TABLE 15

ALLANTOIN-CONTAINING SKIN CREAM WITH CARBOXYPOLYMETHYLENE POLYMER WITH HIGH ALLANTOIN CONCENTRATION

| INGREDIENT | RANGE | OPTIMUM |
|---|---|---|
| Part A | | |
| Water | 50.0-90.0 | 66.05 |
| Carboxypolymethylene Polymer | 0.40-3.0 | 1.00 |
| Propylene Glycol | 2.0-9.0 | 5.70 |
| Part B | | |
| Lanolin Oil | 5.0-15.0 | 10.00 |
| Cetyl Alcohol | 1.0-8.0 | 3.00 |
| Cod Liver Oil | 1.0-7.0 | 2.00 |
| Butylated Hydroxytoluene | 0.10-1.0 | 0.50 |
| Part C | | |
| Methylparaben | 0.10-0.50 | 0.30 |
| Propylparaben | 0.10-0.50 | 0.25 |
| Allantoin | 0.50-10.0 | 9.00 |
| Fragrance | 0.05-0.50 | 0.20 |
| Part D | | |
| Triethanolamine (99%) | 0.05-3.0 | 0.80 |

Example 14

Preparation of a Cream Containing Allantoin with Polyethylene Glycol Ethers of Cetearyl Alcohol with High Allantoin Concentration An OTC skin cream containing allantoin is prepared using the ingredients in Table 16 to provide a cream with an allantoin concentration of about 9.00% with polyethylene glycol ethers of cetearyl alcohol. The skin cream is prepared according to the method of Example 6. The citric acid is added to adjust the pH.

TABLE 16

ALLANTOIN-CONTAINING SKIN CREAM WITH POLYETHYLENE GLYCOL ETHERS OF CETEARYL ALCOHOL WITH HIGH ALLANTOIN CONCENTRATION

| INGREDIENT | RANGE | OPTIMUM |
|---|---|---|
| Part A | | |
| Water | 50.0-90.0 | 58.83 |
| Propylene Glycol | 2.0-9.0 | 5.70 |
| Tetrasodium EDTA | 0.05-0.50 | 0.15 |
| Ceteareth-25 | 0.50-4.0 | 2.60 |
| Citric Acid | 0.04-0.40 | 0.12 |
| Part B | | |
| Lanolin Oil | 5.0-15.0 | 10.60 |
| Cetyl Alcohol | 3.0-10.0 | 4.30 |
| Stearyl Alcohol | 1.0-5.0 | 3.50 |
| Ceteareth-6 | 0.50-4.0 | 1.80 |
| Cod Liver Oil | 1.0-7.0 | 2.00 |
| Butylated Hydroxytoluene | 0.10-1.0 | 0.50 |
| Part C | | |
| Methylparaben | 0.10-0.50 | 0.30 |
| Propylparaben | 0.10-0.50 | 0.25 |
| Diazolidinyl Urea | 0.05-0.50 | 0.15 |
| Allantoin | 0.50-10.0 | 9.00 |
| Fragrance | 0.05-0.50 | 0.20 |

Example 15

Preparation of a Cream Containing Allantoin with Polyethylene Glycol Ethers of Stearic Acid and Glyceryl Stearate with High Allantoin Concentration An OTC skin cream containing allantoin is prepared using the ingredients in Table 17 to provide a cream with an allantoin concentration of about 9.00% with polyethylene glycol ethers of stearic acid and glyceryl stearate. The skin cream is prepared according to the method of Example 7. The citric acid is added to adjust the pH.

TABLE 17

ALLANTOIN-CONTAINING SKIN CREAM WITH POLYETHYLENE GLYCOL ESTER OF STEARIC ACID AND GLYCERYL STEARATE WITH HIGH ALLANTOIN CONCENTRATION

| INGREDIENT | RANGE | OPTIMUM |
|---|---|---|
| Part A | | |
| Water | 50.0-90.0 | 60.36 |
| Propylene Glycol | 2.0-9.0 | 5.70 |
| Tetrasodium EDTA | 0.05-0.50 | 0.15 |
| Citric Acid | 0.04-0.40 | 0.14 |
| PEG-100 Stearate | 1.0-5.0 | 2.60 |
| Part B | | |
| Lanolin Oil | 5.0-15.0 | 10.60 |
| Cetyl Alcohol | 3.0-10.0 | 4.30 |
| Stearyl Alcohol | 1.0-5.0 | 3.50 |
| Glyceryl Stearate | 1.0-5.0 | 2.50 |
| Cod Liver Oil | 1.0-7.0 | 2.00 |
| Butylated Hydroxytoluene | 0.10-1.0 | 0.50 |
| Part C | | |
| Methylparaben | 0.10-0.50 | 0.30 |
| Propylparaben | 0.10-0.50 | 0.25 |
| Diazolidinyl Urea | 0.05-0.50 | 0.20 |
| Allantoin | 0.50-10.0 | 9.00 |
| Fragrance | 0.05-0.50 | 0.20 |

Example 16

Preparation of a Cream Containing Allantoin with a Carboxypolymethylene Polymer and a Polyethylene Glycol Ether of Stearic Acid with High Allantoin Concentration An OTC skin cream containing allantoin is prepared using the ingredients in Table 18 to provide a cream with an allantoin concentration of about 9.00% with a carboxypolymethylene polymer and a polyethylene glycol ester of stearic acid. The skin cream is prepared according to the method of Example 8. The triethanolamine is added to adjust the pH.

TABLE 18

ALLANTOIN-CONTAINING SKIN CREAM WITH A CARBOXYPOLYMETHYLENE POLYMER AND A POLYETHYLENE GLYCOL ESTER OF STEARIC ACID WITH HIGH ALLANTOIN CONCENTRATION

| INGREDIENT | RANGE | OPTIMUM |
|---|---|---|
| Part A | | |
| Water | 50.0-90.0 | 62.45 |
| Carboxypolymethylene Polymer | 0.30-3.0 | 0.85 |
| Propylene Glycol | 2.0-9.0 | 5.70 |
| PEG-100 Stearate | 0.25-2.5 | 1.50 |

TABLE 18-continued

ALLANTOIN-CONTAINING SKIN CREAM WITH A
CARBOXYPOLYMETHYLENE
POLYMER AND A POLYETHYLENE GLYCOL ESTER OF
STEARIC ACID WITH HIGH ALLANTOIN CONCENTRATION

| INGREDIENT | RANGE | OPTIMUM |
|---|---|---|
| Part B | | |
| Lanolin Oil | 5.0-15.0 | 10.60 |
| Cetyl Alcohol | 1.0-8.0 | 4.20 |
| Stearyl Alcohol | 0.50-6.0 | 1.50 |
| Cod Liver Oil | 1.0-7.0 | 2.00 |
| Butylated Hydroxytoluene | 0.10-1.0 | 0.50 |
| Part C | | |
| Methylparaben | 0.10-0.50 | 0.30 |
| Propylparaben | 0.10-0.50 | 0.25 |
| Diazolidinyl Urea | 0.05-0.25 | 0.15 |
| Allantoin | 0.50-9.0 | 9.00 |
| Fragrance | 0.05-0.50 | 0.20 |
| Part D | | |
| Triethanolamine (99%) | 0.05-3.0 | 0.80 |

Example 17

Preparation of a Cream Containing Allantoin with Galactoarabinan, Sodium Lauryl Sulfate, and Beeswax with High Allantoin Concentration An OTC skin cream containing allantoin is prepared using the ingredients in Table 19 to provide a cream with an allantoin concentration of about 9.00% with galactoarabinan, sodium lauryl sulfate, and beeswax. The skin cream is prepared according to the method of Example 9. The citric acid is used to adjust the pH. Another acidic wax can substitute for beeswax.

TABLE 19

COMPOSITION OF ALLANTOIN-CONTAINING SKIN
CREAM WITH GALACTOARABINAN, SODIUM
LAURYL SULFATE, AND BEESWAX
WITH HIGH ALLANTOIN CONCENTRATION

| INGREDIENT | RANGE | OPTIMUM |
|---|---|---|
| Part A | | |
| Water | 50.0-90.0 | 54.15 |
| Propylene Glycol | 2.0-9.0 | 5.70 |
| Sodium Lauryl Sulfate (30%) | 0.50-5.0 | 1.90 |
| Tetrasodium EDTA | 0.05-0.30 | 0.15 |
| Galactoarabinan | 1.0-25.0 | 5.00 |
| Citric Acid | 0.05-0.25 | 0.15 |
| Part B | | |
| Lanolin Oil | 5.0-15.0 | 10.60 |
| Cetyl Alcohol | 1.0-8.0 | 4.20 |
| Stearyl Alcohol | 0.50-6.0 | 2.00 |
| Beeswax | 0.50-5.0 | 1.90 |
| Cod Liver Oil | 0.50-15.0 | 2.00 |
| Butylated Hydroxytoluene | 0.10-3.0 | 0.50 |
| Part C | | |
| Methylparaben | 0.10-0.50 | 0.30 |
| Propylparaben | 0.10-0.50 | 0.25 |
| Allantoin | 0.50-10.0 | 9.00 |
| Fragrance | 0.05-0.50 | 0.20 |

Example 18

Preparation of a Cream Containing Allantoin with Sodium Lauryl Sulfate, and Beeswax with High Allantoin Concentration and pH of 3.9

An OTC skin cream containing allantoin is prepared using the ingredients in Table 20 to provide a cream with an allantoin concentration of about 9.00% with a pH of 3.9 with sodium lauryl sulfate and beeswax. The water phase (Part A in Table 20) was heated to 160-180° F. The oil phase (Part B in Table 20) was heated to 160-180° F. The heated oil phase was added to the heated water phase with continuing mixing to form an oil-in-water emulsion when this system was cooled. Between 115-125° F., the Ingredients in Part C of Table 20 were added to the emulsion under high shear mixing. The final 9.00% allantoin cream had a pH of 3.90 and excellent emulsion stability when analyzed after aging 6 months at 40° C. The top, middle, and bottom of the batch were analyzed for allantoin and was found to contain 9.65%, 9.57%, and 9.66% respectively. After standing in a jar for three months at room temperature, the top, middle, and bottom of the jar were analyzed and the allantoin concentration at each point was found to be 9.59%, 9.57, and 9.58% respectively, showing that the allantoin does not precipitate in the jar on standing after manufacture. Analysis of a sample of the 9% allantoin cream after aging at 40° C. for eight months yielded 9.87% allantoin. This is within the specification that the active be within ±10% of its initial level after aging. The slightly higher value of 9.87% may indicate that some water has been lost on aging.

TABLE 20

COMPOSITION OF ALLANTOIN-CONTAINING SKIN CREAM
WITH pH OF 3.9 WITH BEESWAX AND HIGH ALLANTOIN
CONCENTRATION

| INGREDIENT | RANGE | OPTIMUM |
|---|---|---|
| Part A | | |
| Water | 50.0-90.0 | 58.98 |
| Sodium Lauryl Sulfate (30%) | 0.50-5.0 | 3.00 |
| Propylene Glycol | 2.0-9.0 | 5.70 |
| Tetrasodium EDTA | 0.05-0.50 | 0.15 |
| Citric Acid | 0.05-0.50 | 0.12 |
| Part B | | |
| Lanolin Oil | 5.0-15.0 | 10.60 |
| Cetyl Alcohol | 3.0-10.0 | 4.20 |
| Stearyl Alcohol | 1.0-5.0 | 2.00 |
| Beeswax | 0.50-5.0 | 3.00 |
| Part C | | |
| Methylparaben | 0.10-0.50 | 0.30 |
| Propylparaben | 0.10-0.50 | 0.25 |
| Fragrance | 0.05-0.50 | 0.20 |
| Allantoin | 2.50-10.0 | 9.00 |

ADVANTAGES OF THE PRESENT INVENTION

The present invention provides an allantoin-containing composition that is an oil-in-water emulsion using either an acidic anionic polymer and an anionic emulsifier or an acidic anionic polymer and a nonionic emulsifier that is an ethoxylated ether or ethoxylated ester. The composition can further include a carbohydrate polymer that can be polygalactose or polyarabinose. If an ethoxylated ether or ethoxylated ester is used, the composition can further comprise glyceryl stearate.

The composition has improved thermal stability. The composition according to the present invention is useful for treatment of a number of skin diseases and conditions, including epidermolysis bullosa, pressure ulcers, diabetic ulcers, decubitus ulcers, and milia, as well as other inflammatory conditions, such as conditions affecting the skin and having an inflammatory component such as eczema, urticaria, atopic dermatitis, contact dermatitis, arthritis, gout, and lupus erythematosus. Compositions according to the present invention are also useful as skin protectants even when these diseases are not present. Compositions according to the present invention are well tolerated and can be used with other treatments.

Although the present invention has been described in considerable detail, with reference to certain preferred versions thereof, other versions and embodiments are possible. Therefore, the scope of the invention is determined by the following claims.

While the specification describes particular embodiments of the present invention, those of ordinary ski can devise variations of the present invention without departing from the inventive concept.

I claim:

1. A method for treating diabetic ulcers in a patient in need thereof comprising contacting the patient's skin with an effective amount of a composition comprising an oil-in-water emulsion comprising:
   (a) allantoin; and
   (b) an emulsifier system including beeswax and an anionic emulsifier that is substantially hydrophilic and is soluble in water; and
   (c) an acid to adjust the pH of the composition to a pH of about 4.5 to about 5.8,
   wherein the allantoin is stable in the composition for 30 days, 60 days, or 90 days at 40° C.

2. The method of claim 1, wherein the anionic emulsifier is selected from the group consisting of ammonium lauryl sulfate, sodium laureth sulfate, sodium oleyl succinate, ammonium lauryl sulfosuccinate, sodium dodecylbenzenesulfonate, ammonium laureth sulfate, sodium N-lauryl sarcosinate, sodium lauryl sulfate, and combinations thereof.

3. The method of claim 2, wherein the anionic emulsifier is sodium lauryl sulfate.

4. The method of claim 1, wherein the acid comprises at least one organic acid from 2 to 22 carbon atoms.

5. The method of claim 4, wherein the at least one organic acid is selected from the group consisting of citric acid, ascorbic acid, glycolic acid, lactic acid, benzoic acid, salicylic acid, and combinations thereof.

6. The method of claim 1, wherein the acid comprises at least one inorganic acid.

7. The method of claim 6, wherein the at least one inorganic acid is selected from the group consisting of hydrochloric acid, sulfuric acid, phosphoric acid, and combinations thereof.

8. The method of claim 1, wherein the acid comprises at least one organic acid and at least one inorganic acid.

9. The method of claim 1, wherein the allantoin is stable in the composition for 30 days at 40° C.

10. The method of claim 1, wherein the allantoin is stable in the composition for 60 days at 40° C.

11. The method of claim 1, wherein the allantoin is stable in the composition for 90 days at 40° C.

12. The method of claim 1, wherein the composition further comprises an emollient component.

13. The method of claim 12, wherein the emollient component comprises at least one emollient selected from the group consisting of lanolin oil, cetyl alcohol, stearyl alcohol, cod liver oil, butylated hydroxytoluene, and combinations thereof.

14. The method of claim 1, wherein the composition further comprises a preservative component.

15. The method of claim 14, wherein the preservative component comprises at least one preservative selected from the group consisting of methylparaben, ethylparaben, propylparaben, butylparaben, phenoxyethanol, and combinations thereof.

16. The method of claim 1, wherein the composition further comprises a chelating agent.

17. The method of claim 16, wherein the chelating agent is tetrasodium EDTA.

18. The method of claim 1, wherein the composition further comprises a solvent component.

19. The method of claim 18, wherein the solvent component comprises at least one solvent selected from the group consisting of propylene glycol, glycerin, butylene glycol, and combinations thereof.

20. The method of claim 1, wherein the composition further comprises at least one component selected from the group consisting of fragrance, proteins, humectants, essential oils, vitamins, colorants, hydroxyacids, plant extracts, sunscreens, sodium hyaluronate, lipids, fatty acids, thickeners, panthenol, and combinations thereof.

* * * * *